United States Patent
Seon

(10) Patent No.: US 8,066,653 B2
(45) Date of Patent: Nov. 29, 2011

(54) SCOLIOSIS BRACE HAVING ANGLE ADJUSTMENT UNIT

(76) Inventor: Dong Yun Seon, Seoul (KR)

( * ) Notice: Subject to any disclaimer, the term of this patent is extended or adjusted under 35 U.S.C. 154(b) by 400 days.

(21) Appl. No.: 12/271,214

(22) Filed: Nov. 14, 2008

(65) Prior Publication Data

US 2009/0137934 A1    May 28, 2009

(30) Foreign Application Priority Data

Nov. 16, 2007  (KR) .................. 10-2007-0117380
Mar. 7, 2008   (KR) .................. 10-2008-0021335

(51) Int. Cl.
*A61F 5/00*    (2006.01)
(52) U.S. Cl. ............................ 602/19; 602/5
(58) Field of Classification Search ............... 602/5, 18, 602/19; 2/44, 45; 128/869, 870
See application file for complete search history.

(56) References Cited

U.S. PATENT DOCUMENTS 5,449,338 A  *  9/1995  Trudell ................... 602/19
5,503,621 A  *  4/1996  Miller .................... 602/19

FOREIGN PATENT DOCUMENTS

| JP | 01-016503 U | 9/1990 |
| JP | 2001-083882 A | 3/2001 |
| JP | 2001-137269 A | 5/2001 |
| JP | 2005-137448 A | 6/2005 |
| JP | 2006-211091 A | 8/2006 |

OTHER PUBLICATIONS

Japanese Patent Office, Japanese Office Action issued in corresponding JP Application No. 2008-292487, dated Apr. 19, 2011.
Korean Office Action issued in 10-2008-0021335on Nov. 26, 2009.

* cited by examiner

*Primary Examiner* — Michael A. Brown
(74) *Attorney, Agent, or Firm* — Sughrue Mion, PLLC

(57) ABSTRACT

Disclosed is a scoliosis brace having an angle adjustment unit and a plurality of support units connected to one another so that the relative position can be changed to support different parts of a human body. The body is pressurized according to the relative position of respective support units so that the spinal column is corrected precisely.

15 Claims, 20 Drawing Sheets

SCOLIOSIS BRACE HAVING ANGLE ADJUSTMENT UNIT

CROSS-REFERENCE TO RELATED APPLICATIONS

This application claims priority under 35 U.S.C. §119 to Korean Patent Application No. 10-2007-0117380, filed in Korea on Nov. 16, 2007, and Korean Patent Application No. 10-2008-0021335, filed in Korea on Mar. 7, 2008, the entirety of which are hereby incorporated by reference.

BACKGROUND OF THE INVENTION

1. Field of the Invention

The present invention relates to a scoliosis brace having an angle adjustment unit, and more particularly to a scoliosis brace adapted to freely adjust the correction angle according to the curvature of the spinal column of a scoliosis patient so that the patient can be treated efficiently.

2. Description of the Prior Art

As generally known in the art, scoliosis is derived from Greek skolios meaning crooked, and refers to a medical condition in which a person's spinal column is curved from side to side. A healthy person's spinal column constitutes a straight line together with the head and legs when viewed from the front or back. However, some people's spinal column has a lateral curve for various reasons. Scoliosis includes functional scoliosis, which results from bad postures or trauma but involves no structural change of the spinal column, and structural scoliosis, which involves a structural change of the spinal column. In many cases, little is known about the cause of the structural scoliosis, which tends to worsen gradually and may even degrade the function of the heart or lungs.

Treatment of scoliosis includes brace-based treatment, which is usually selected when the angle of curvature is 20-40°, and surgical treatment. Braces for scoliosis include a Milwaukee brace, which extends up to the neck, a thoracolumbo brace, which extends below the armpits, etc.

Such conventional braces for treating scoliosis include a support unit for protecting the patient's waist and a retaining unit for retaining the support unit on the waist. The support unit defines an inwardly curved surface, which is maintained by a number of reinforcement straps embedded in the support unit. The retaining unit has an auxiliary band, to which Velcro is attached.

When such a scoliosis brace is worn, the reinforcement straps embedded in the support unit accurately supports the lumbar vertebrae, and the Velcro of the retaining unit firmly retains the brace to apply pressure to the lumbar vertebra at a predetermined angle.

However, the conventional scoliosis brace has a problem in that, since each scoliosis patient has a different curvature of the spinal column, the degree of improvement that can be expected when the brace having a fixed correction angle is worn is limited. Furthermore, it requires a large amount of money, time, and effort to provide a brace having a correction angle customized to each patient.

SUMMARY OF THE INVENTION

Accordingly, the present invention has been made to solve the above-mentioned problems occurring in the prior art, and the present invention provides a scoliosis brace adapted to freely adjust the correction angle according to the curvature of the spinal column of a scoliosis patient so that the patient can be treated in an optimized manner.

In accordance with an aspect of the present invention, there is provided a scoliosis brace including a plurality of support units for supporting different parts of a human body, the support units being connected to one another so that relative positions can be changed, wherein the human body is pressurized according to relative positions of respective support units to correct the spinal column.

In accordance with another aspect of the present invention, the plurality of support units includes an upper support unit for receiving and supporting the upper part of the body; a middle support unit for receiving and supporting the middle part of the body; and a lower support unit for receiving and supporting the lower part of the body, and respective support units are connected to one another so that relative positions can be modified, and the upper, middle, and lower parts of the body are pressurized according to relative positions of respective support units, to generate pressurization force for correcting the spinal column.

In accordance with another aspect of the present invention, the scoliosis brace further includes at least one first rod having a first end rotatably connected to the upper support unit; at least one second rod having a first end rotatably connected to the lower support unit; and an angle adjustment unit attached to the middle support unit, second ends of the first and second rods being rotatably connected to the angle adjustment unit, respectively, so that rotation angles of the first and second rods can be adjusted.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE EXEMPLARY EMBODIMENTS

Figure 1:
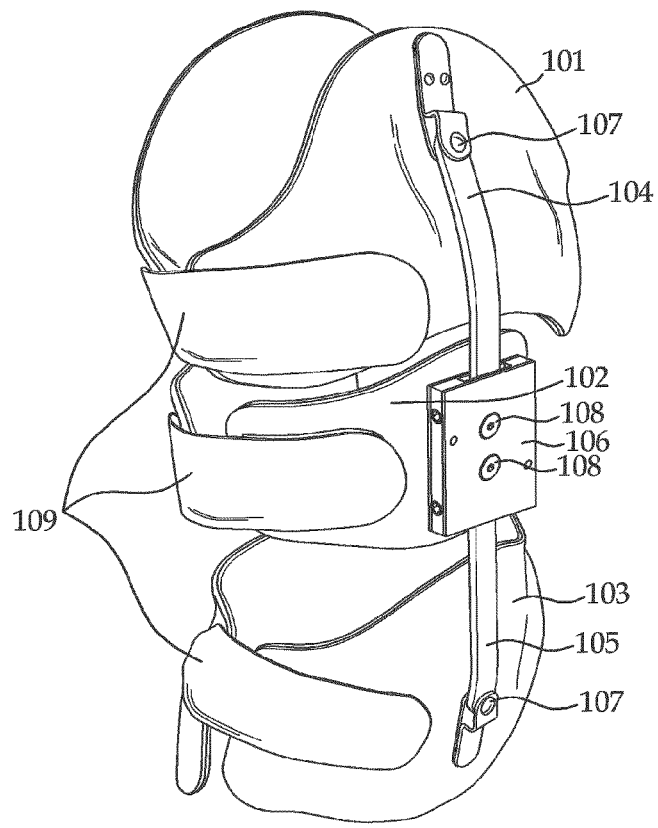
FIG. 1 is an assembled perspective view of a scoliosis brace according to a first embodiment of the present invention.

Hereinafter, an exemplary embodiment of the present invention will be described with reference to the accompanying drawings. In the following description and drawings, the same reference numerals are used to designate the same or similar components, and so repetition of the description on the same or similar components will be omitted.

A scoliosis brace according to the present invention includes an upper support unit 101 adapted to make a direct contact with the human body; a middle support unit 102; a lower support unit 103; at least one first and second rods 104 and 105 for connecting between the support units; and an angle adjustment unit 106 attached to the middle support unit 102 to adjust the angle of the first and second rods 104 and 105.

The upper support unit 101 of the scoliosis brace according to the present invention is adapted to support the thoracic vertebrae of the human body; the middle support unit 102 is adapted to support the lower thoracic vertebrae and the lumbar vertebrae; and the lower support unit 103 is adapted to support the lower lumbar vertebrae and the sacrum.

Conventional vertebral braces usually have a single unit adapted to contact the human body, and the part for supporting lumbar vertebrae is bent inward at a predetermined angle. Even when a conventional vertebral brace consists of three parts for supporting the thorax, loin, and sacrum, respectively, these three parts are fixed at a predetermined angle. In this case, the lumbar support part simply applies force to the thoracic or lumbar by bands, for example.

However, the scoliosis brace according to the present invention can easily adjust the angle of the first and second rods 104 and 105 by the angle adjustment unit 106 so that the three units (i.e. upper, middle, and lower support units 101, 102, and 103) can be freely adjusted to have a predetermined angle according to the curvature of the spinal column of the patient, as well as to which part of the spinal column they support, and then retained in that condition.

Therefore, when a scoliosis patient wears the scoliosis brace according to the present invention, the brace can be adapted to pressurize the curved part and correct the spinal column while the brace is worn by the patient, unlike the conventional integral braces. Furthermore, the inventive brace can maintain a desired correction angle, unlike the conventional band pressurizing type, so that the spinal column is constantly pressurized and corrected as desired.

The fact that the correction angle can be easily adjusted while the brace is worn by the patient makes it possible to easily change the correction method as the patient's condition improves or worsens.

Figure 2:
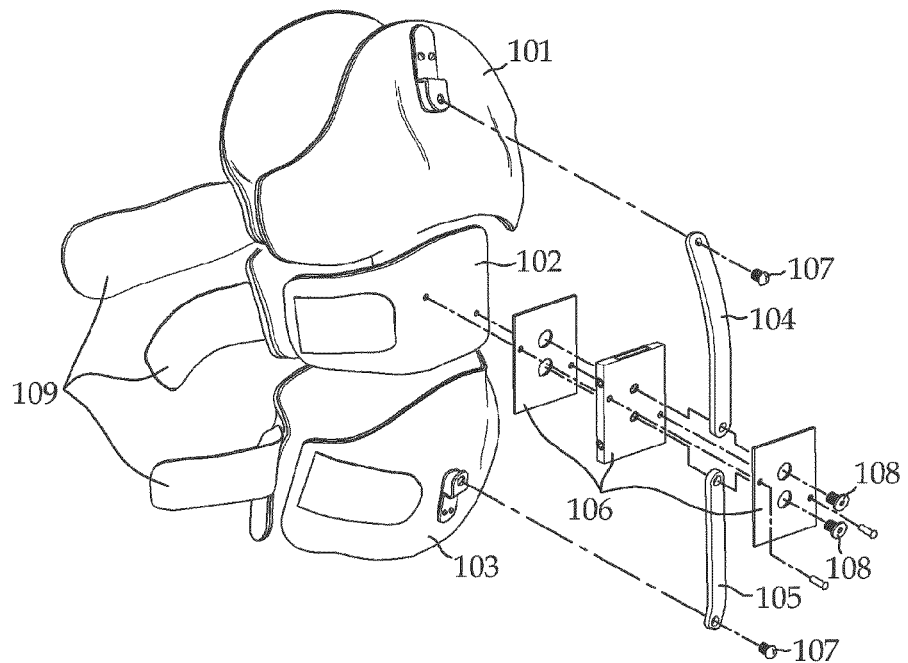
FIG. 2 is an exploded perspective view of the scoliosis brace shown in FIG. 1.

Referring to FIGS. 1 and 2, a scoliosis brace according to a first embodiment of the present invention includes an upper support unit 101 shaped to surround the thorax of the human body; a lower support unit 103 shaped to surround the sacrum; a middle support unit 102 shaped to surround the loin from one side; a first rod 104 for connecting the upper and middle support units 101 and 102 with one end of the first rod 104 rotatably connected to the upper support unit 101 by a hinge shaft 107, for example; a second rod 105 for connecting the lower and middle support units 103 and 102 with one end of the second rod 105 rotatably connected to the lower support unit 103 by a hinge shaft 107, for example; and an angle adjustment unit 106 attached to the middle support unit 102. The other ends of the first and second rods 104 and 105 are rotatably connected to the angle adjustment unit 106 by hinge shafts 108, for example.

The upper, middle, and lower support units 101, 102, and 103 have an opening formed on one side so that the human body can pass through. After the brace is mounted on the body through the opening, a fastening means, such as Velcro 109, completely fixes the brace to the upper part of the body.

Those skilled in the art can understand that, although the first and second rods 104 and 105 are shown in FIGS. 1-3B on both the front and rear surfaces of the upper, middle, and lower support units 101, 102, and 103 to connect them, the present invention is not limited to the construction shown in FIGS. 1-3B. Particularly, the first and second rods 104 and 105 may be positioned on only one of the front and rear surfaces of the upper, middle, and lower support units 101, 102, and 103. Furthermore, at least three first and second rods 104 and 105 may be used for connection regardless of the position.

Figure 3A:
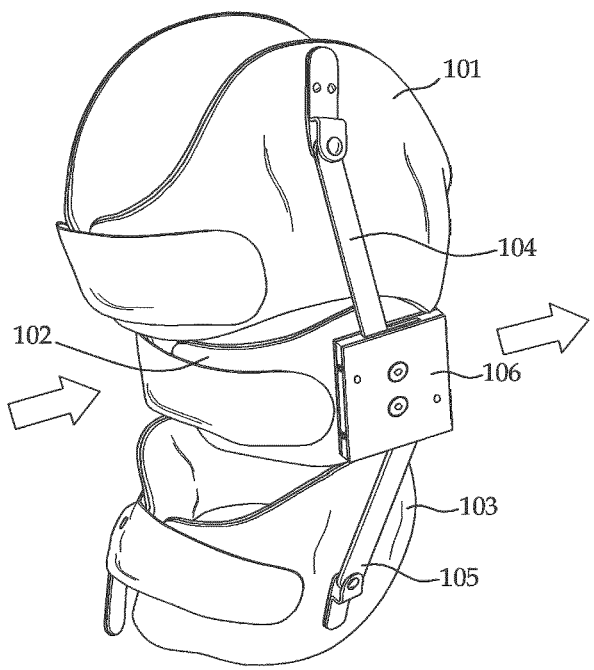
FIGS. 3A and 3B show the process of operating the scoliosis brace shown in FIG. 1.
Figure 3B:
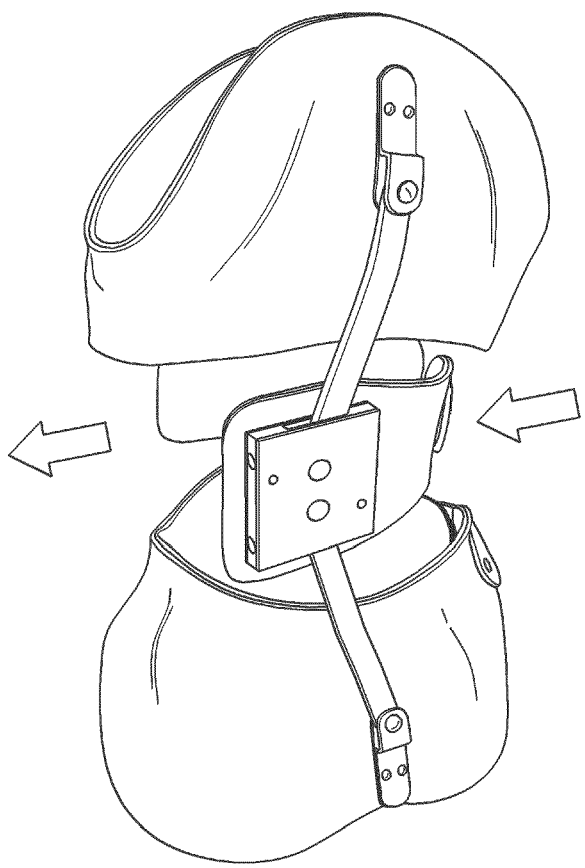

Referring to FIGS. 3A and 3B, the angle adjustment unit 106 (described later) adjusts the angle of the first and second rods 104 and 105 according to the patient's condition in the following manner. The middle support unit 102, to which the angle adjustment unit 106 is attached, does not lie on the same straight line as the upper and lower support units 101 and 103. Instead, the middle support unit 102 is adjusted and retained so that it deviates from a virtual line joining the upper and lower support units 101 and 103. After the angle of the scoliosis brace is adjusted, it is worn by the patient and firmly retained. Then, the curved part of the spinal column of the patient is pressurized constantly in a direction opposite to the curved direction so that the spinal column is corrected.

As such, the correction angle of the scoliosis brace can be adjusted by the angle adjustment unit 106 according to the curvature of the spinal column of the patient. In addition, the angle adjustment unit 106 can be adjusted according to the direction of curvature of the spinal column, or the brace can be worn in a different direction.

For example, it will be assumed that the middle support unit 102 of the scoliosis brace is adapted to support the middle part of the human body, particularly the lower thoracic vertebrae and one side of the lumbar vertebrae, as shown in FIGS. 1-3B. Then, according to whether the spinal column of the patient is curved in the leftward or rightward direction, the patient wears the brace so that either its front or rear surface can be seen from the front. Furthermore, when the middle support unit 102 of the scoliosis brace is adapted to surround the middle part of the human body, particularly all of the lower thoracic vertebrae and lumbar vertebrae (not shown in the drawings), the middle support unit 102 can be positioned to the left or right simply by adjusting the angle adjustment unit 106.

In the case of a scoliosis brace having a middle support unit 102 adapted to support the middle part of the human body, particularly the lower thoracic vertebrae and one side of the lumbar vertebrae, as shown in FIGS. 1-3B, it can be initially fabricated either for a patient having a left curvature or a patient having a right curvature.

Furthermore, the scoliosis brace according to the present invention is of a three-piece type, i.e. it has upper, middle, and lower support units 101, 102, and 103, unlike conventional braces of an integral type. Therefore, the inventive brace can pressurize the spinal column at three points (i.e. thorax, loin, and sacrum), and exhibits a far better correction effect.

The angle adjustment unit 106 of the scoliosis brace according to the first embodiment of the present invention may include a base member 112, to which the other ends of the first and second rods 104 and 105 are rotatably connected, respectively, and which has at least one insertion hole 110 formed thereon, and an adjustment member 111 inserted into the insertion hole 110 to adjust the angle of at least one of the first and second rods 104 and 105.

Figure 4A:
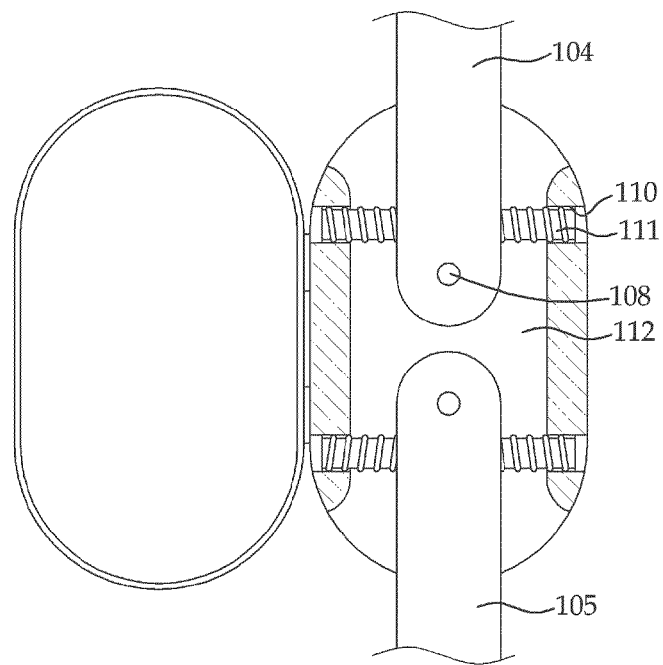
FIGS. 4A-4C are sectional views showing the process of operating an angle adjustment unit of the scoliosis brace shown in FIG. 1.

FIG. 4A is a sectional view of the angle adjustment unit 106 of the scoliosis brace according to the first embodiment of the present invention. Referring to FIG. 4A, the other ends of the first and second rods 104 and 105 are rotatably connected to the base member 112 by hinge shafts 108, for example. The base member 112 has at least one insertion hole 110 formed on both lateral surfaces so that an adjustment member 111 (e.g. adjustment screw) is inserted through the insertion hole 110 to adjust the angle of the first and second rods 104 and 105. In order to guarantee smooth rotation of the first and second rods 104 and 105, the insertion hole 110 and the adjustment member 111 are preferably positioned so that they are not parallel with the hinge shafts 108, which connect the first and second rods 104 and 105 to the base member 112.

Figure 4B:
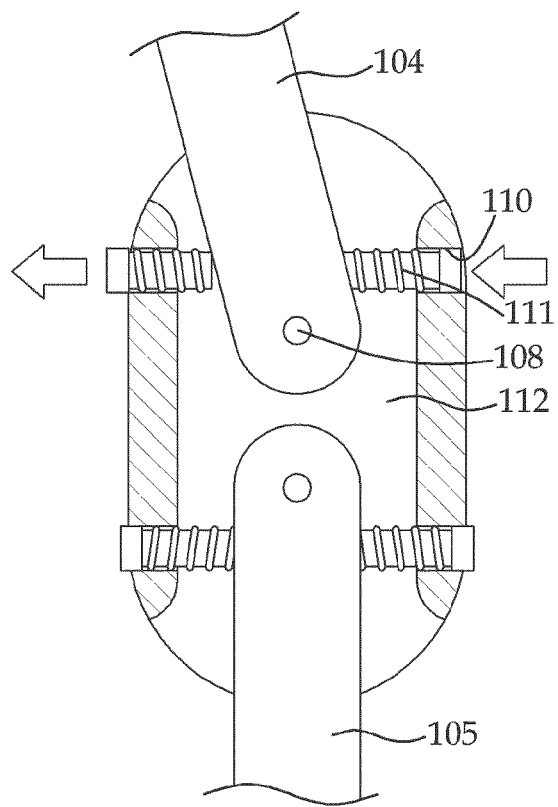
Figure 4C:
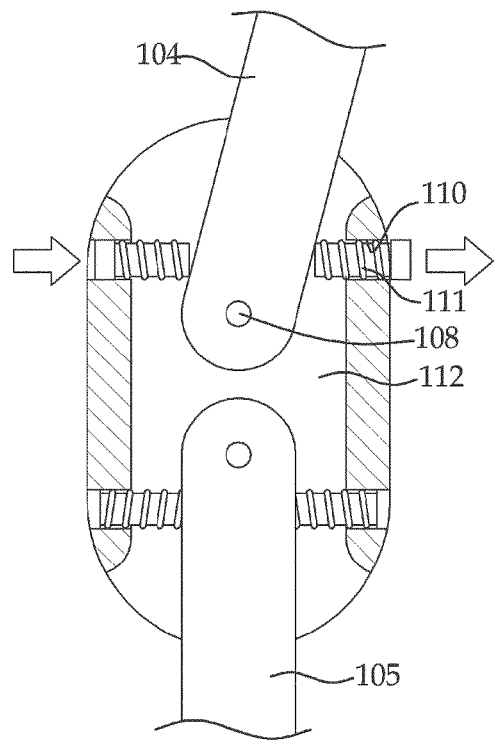

FIGS. 4B and 4C show the process of operating the angle adjustment unit 106 of the scoliosis brace according to the first embodiment of the present invention. Referring to FIGS. 4B and 4C, the adjustment members 111 are screw-coupled to the insertion holes 110 so that they can move linearly in the leftward/rightward direction according to the direction of rotation of the screws. The first and second rods 104 and 105 are pressurized by the leftward/rightward movement of the adjustment members 111, and are allowed to rotate by a predetermined angle about the hinge shafts 108 connected to the base member 112. The angle of the first and second rods 104 and 105 is adjusted in this manner.

More particularly, as shown in FIG. 4B, the left adjustment member 111 is unfastened to move it backward, and the right adjustment member 111 is fastened to move it forward. Then, the first rod 104 is pressurized in the leftward direction and is slanted in the same direction. As such, the angle of the first rod 104 can be adjusted as desired by adjusting the degree of pressurization by the adjustment members 111.

As shown in FIG. 4C, the angle of the first rod 104 can be adjusted so that it is slanted in the rightward direction in the same manner as shown in FIG. 4B. The same adjustment method can be applied to the second rod 105.

After adjusting the angle of the first rod 104 so that it is slanted to the left, as show in FIG. 4B, the left adjustment member 111 is unfastened a little so that, although the first rod 104 is not allowed to rotate further clockwise, it can rotate to some degree counterclockwise. In this case, the middle support unit, to which the angle adjustment unit 106 is attached, pressurizes the spinal column in the rightward direction. Particularly, the movement of the middle support unit 102 in a direction opposite to the pressurizing direction (i.e. leftward direction) is limited, but the middle support unit 102 is allowed to move in the rightward direction. As a result, the brace wearer can move more freely to lessen the constraint resulting from wearing the brace and stretch muscles to some extent. Another example of the angle adjustment unit, the rotation of which in only one direction is limited, will be described later.

Figure 5:
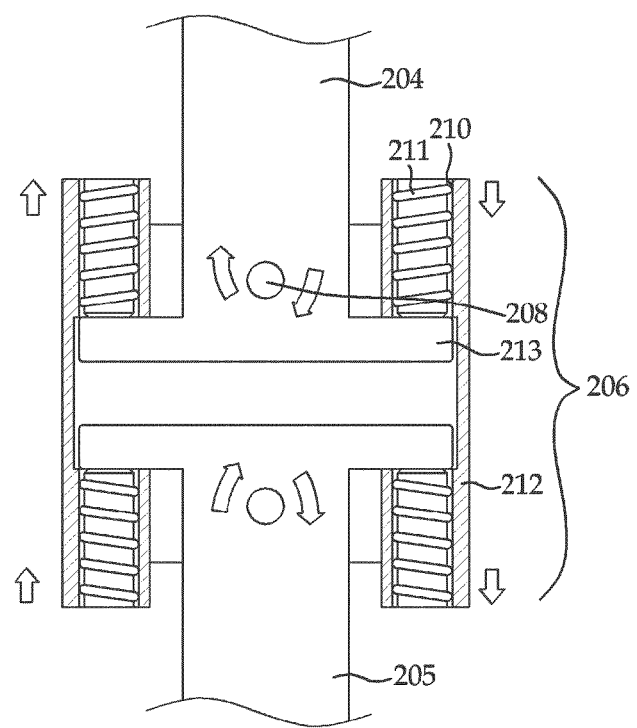
FIG. 5 is a sectional view briefly showing an angle adjustment unit of a scoliosis brace according to a second embodiment of the present invention.

Referring to FIG. 5, a scoliosis brace according to a second embodiment of the present invention includes an angle adjustment unit 206, which is constructed as follows. The other end of at least one of the first and second rods 204 and 205 has an engaging step 213 extending in a direction perpendicular to the longitudinal direction of at least one of the first and second rods 204 and 205. The adjustment member 211 may be installed in parallel with at least one of the first and second rods 204 and 205 to pressurize the engaging step 213.

However, the insertion hole 210, to which the adjustment member 211 is screw-coupled, is preferably positioned at a sufficient interval from the first and second rods 204 and 205 so that the angle of rotation of the first and second rods 204 and 205 is not limited.

The adjustment members 211, which are installed in parallel with the first and second rods 204 and 205, pressurize the engaging steps 213, which are perpendicular to the other ends of the first and second rods 204 and 205, so that the first and second rods 204 and 205 are rotated. By unfastening the adjustment member 211, which lies to the left of the first rod 204, to move it backward, and by fastening the adjustment member 211 on the right side to move it forward, the first rod 204 is rotated clockwise and slanted to the right so that its angle is adjusted as desired.

Except that the insertion holes 210 and the adjustment members 211 are installed in parallel with the first and second rods 204 and 205 to pressurize the engaging steps on the other ends of the first and second rods 204 and 205, the scoliosis brace according to the second embodiment of the present invention has the same construction as that of the above-mentioned scoliosis brace according to the first embodiment.

Figure 6:
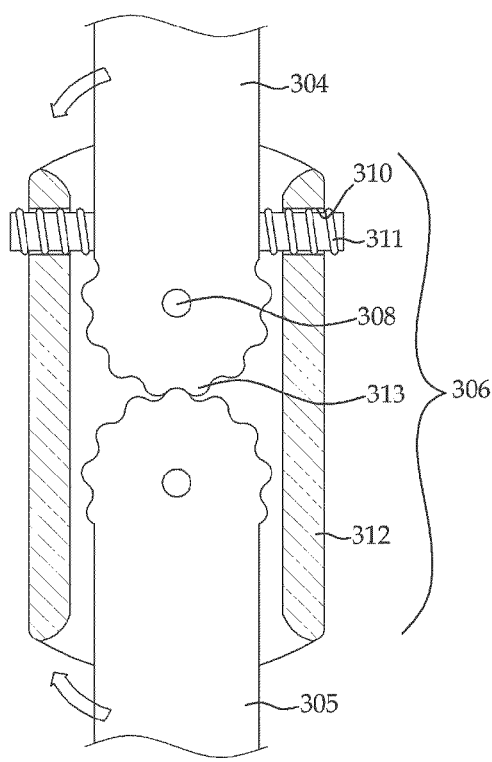
FIG. 6 is a sectional view briefly showing an angle adjustment unit of a scoliosis brace according to a third embodiment of the present invention.

Referring to FIG. 6, a scoliosis brace according to a third embodiment of the present invention has an angle adjustment unit 306 configured so that the first and second rods 304 and 305 are coupled to and interlocked with each other. Particularly, the other ends of the first and second rods 304 and 305 are coupled by gears 313.

Except that the other ends of the first and second rods 304 and 305 are coupled by gears 313 to interlock with each other, the scoliosis brace according to the third embodiment of the present invention has the same construction as the above-mentioned first and second embodiments. Particularly, if the adjustment member 311, which is screw-coupled to the insertion hole 310, adjusts the angle of the first rod 304 to slant it to the right, the second rod 305 slants to the right and changes the angle in an interlocked manner because the gears 313 formed on the other ends of the first and second rods 304 and 305 mesh with each other.

If the other ends of the first and second rods 304 and 305 are coupled at a gear ratio of 1:1, the first and second rods 304 and 305 are adjusted by the same angle. If the gear ratio is varied, the first and second rods 304 and 305 are adjusted by different angles.

Figure 7:
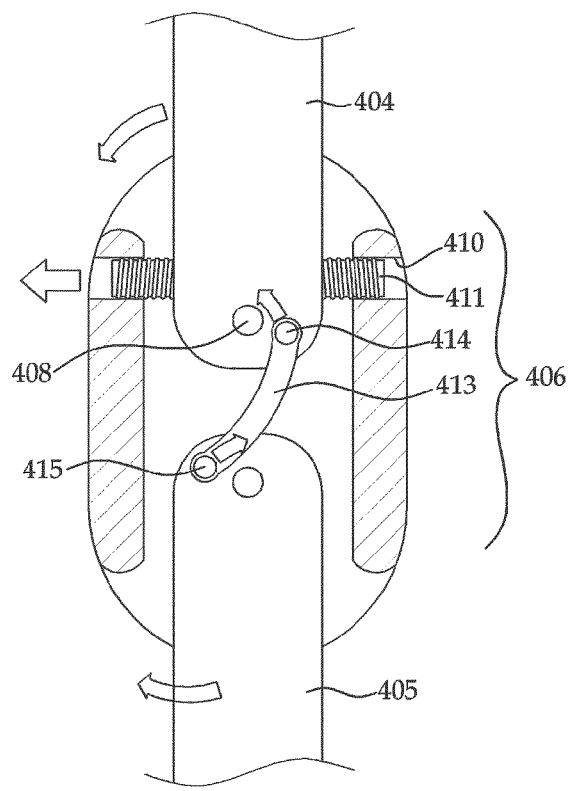
FIG. 7 is a sectional view briefly showing an angle adjustment unit of a scoliosis brace according to a fourth embodiment of the present invention.

Referring to FIG. 7, a scoliosis brace according to a fourth embodiment of the present invention has an angle adjustment unit 406 configured as follows. The first and second rods 404 and 405 are coupled to and interlocked with each other by a connection member 413. One end 414 of the connection member 413 is rotatably connected to the other end of the first rod 404, and the other end 415 of the connection member 413 is rotatably connected to the other end of the second rod 405.

Except that the first and second rods 404 and 405 are interlocked with each other by the connection member 413, the scoliosis brace according to the fourth embodiment of the present invention has the same construction as the above-mentioned first and second embodiments.

If the first rod 404 is rotated counterclockwise by the adjustment members 411 screw-coupled to the insertion holes 410, the hinge shaft 414, which connects the other end of the first rod 404 to the connection member 413, rotates in the same direction. The rotation of the hinge shaft 414 is converted by the connection member 413 into force that pulls the hinge shaft 415, which connects the other end of the second rod 405 to the connection member 413. Then, the second rod 405 is rotated counterclockwise about the hinge shaft 408. As such, the angle of the second rod 405 is adjusted based on interlocking with the first rod 404.

Figure 8:
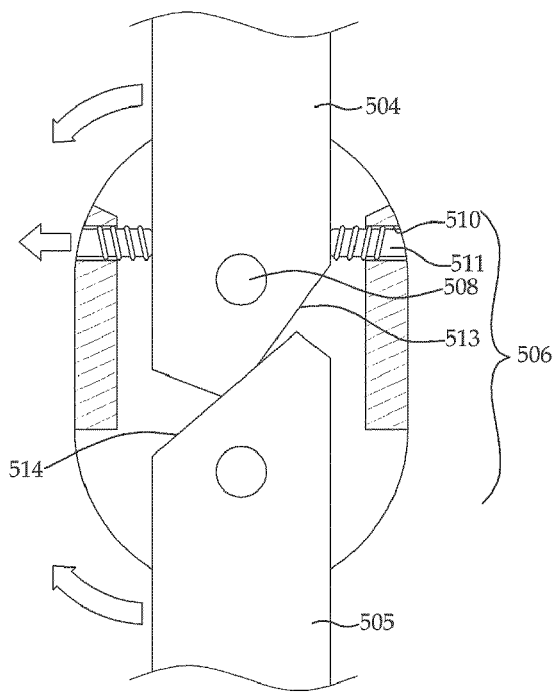
FIG. 8 is a sectional view briefly showing an angle adjustment unit 506 of a scoliosis brace according to a fifth embodiment of the present invention.

Referring to FIG. 8, a scoliosis brace according to a fifth embodiment of the present invention has an angle adjustment unit 506 configured so that the first and second rods 504 and 505 are coupled to and interlocked with each other. Particularly, the first and second rods 504 and 505 have chamfers 513 and 514 formed on the other ends so that the chambers 513 and 514 face and contact each other.

Except that the first and second rods 504 and 505 have chamfers 513 and 514 formed on the other ends so that the chambers 513 and 514 face and contact each other, the scoliosis brace according to the fifth embodiment of the present invention has the same construction as the above-mentioned first and second embodiments.

If the first rod 504 is rotated counterclockwise by the adjustment members 511 inserted into the insertion holes 510, the chamfer 513 formed on the other end of the first rod 504 rotates and pushes the chamfer 514 of the second rod 505, which has been facing and contacting the chamfer 513. As a result, the second rod 505 is rotated counterclockwise, and its angle is adjusted based on interlocking with the first rod 504.

In the case of the interlocking structure according to the eighth embodiment show in FIG. 8, interlocking is possible with regard to rotation in such a direction that the chamfers 513 and 514 of the first and second rods 504 and 505 push each other (i.e. counterclockwise rotation of the first rod), but no rotational force is transmitted with regard to rotation in such a direction that the chamfers 513 and 514 move away from each other (i.e. clockwise rotation of the first rod). If a scoliosis brace is equipped with the above-mentioned angle adjustment unit 506, rotation of the middle support unit in one direction is limited, but it is allowed to freely rotate in the other direction. If a scoliosis patient wears this brace, movement in a direction requiring pressurization for correction is limited, but the patient can freely move in the opposite direction. This lessens the degree of constraint that the patient may feel while wearing the brace to some extent. Considering that a scoliosis brace has only to apply pressure on one side, the construction according to the present embodiment (i.e. angle adjustment and retaining are possible on one side) has the same functionality and effect of correction as when both sides are retained.

Those skilled in the art can understand that, when the first and second rods are adapted to interlock with each other as in the case of the third to fifth embodiments shown in FIGS. 6-8, the adjustment members 311, 411, and 511 for adjusting the angle of the rods, as well as the insertion holes 310, 410, and 510, to which the adjustment members are screw-coupled, are not necessarily formed on both sides of the first and second rods (of course, this construction is not excluded), and may be formed on only one side thereof.

Figure 9:
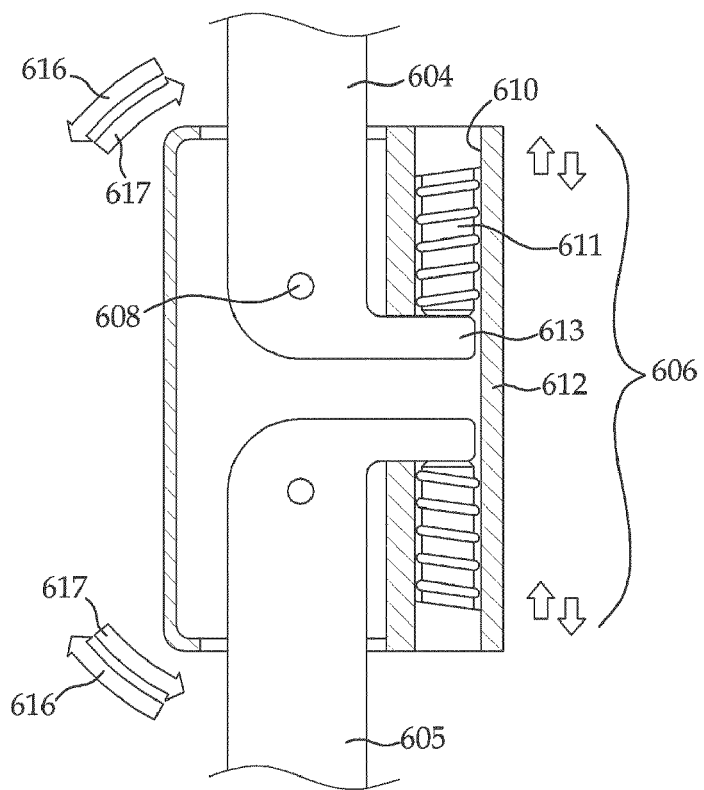
FIG. 9 is a sectional view briefly showing an angle adjustment unit of a scoliosis brace according to a sixth embodiment of the present invention.

Referring to FIG. 9, a scoliosis brace according to a sixth embodiment of the present invention has an angle adjustment unit 606 configured so that the adjustment member 611 is solely fastened to the insertion hole 610 formed on one side of at least one of the first and second rods 604 and 605 to allow rotation 617 of the first and second rods 604 and 605 in one direction but limit rotation 616 in the other direction.

The other ends of the first and second rods 604 and 605 are rotatably connected to the base member 612 by hinge shafts 608, for example. An engaging step 613 is formed on one side of the other end of at least one of the first and second rods 604 and 605 so as to extend in a direction perpendicular to the longitudinal direction of the first and second rods 604 and 605. The insertion hole 610 and the adjustment member 611 (e.g. adjustment screw) screw-coupled to it are installed in parallel with the first and second rods 604 and 605 on the same side on which the engaging step 613 is formed. As a result, the adjustment member 611, when screw-rotated, pressurizes the engaging step 613 and rotates the first and second rods 604 and 605.

It is to be noted that, although the engaging step 613 limits counterclockwise rotation 616 of the first rod 604 and clockwise rotation 616 of the second rod 605, it allows clockwise rotation 617 of the first rod 604 and counterclockwise rotation 617 of the second rod 605. The operation and advantage of the angle adjustment unit, which limits rotation in only one direction, according to the sixth embodiment are the same as described with regard to the fifth embodiment.

Figure 10:
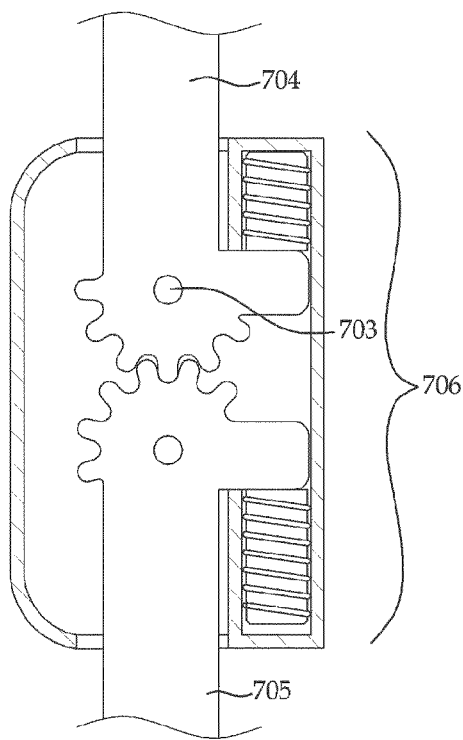
FIG. 10 is a sectional view briefly showing an angle adjustment unit of a scoliosis brace according to a seventh embodiment of the present invention.

Referring to FIG. 10, a scoliosis brace according to a seventh embodiment of the present invention has an angle adjustment unit 706 having the same construction as the sixth embodiment described with reference to FIG. 9, except that the other ends of the first and second rods 704 and 705 are gear-coupled to and interlocked with each other. The structure of interlocking between the first and second rods 704 and 705 may be the same as the above-mentioned third embodiment.

Figure 11:
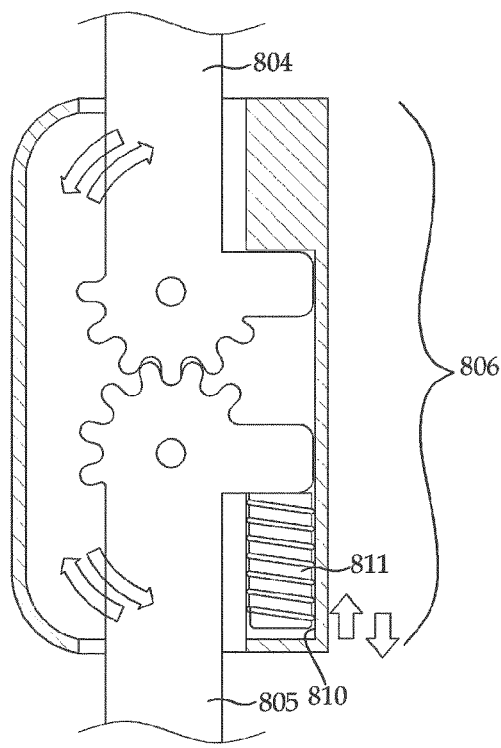
FIG. 11 is a sectional view briefly showing an angle adjustment unit of a scoliosis brace according to an eighth embodiment of the present invention.

Referring to FIG. 11, a scoliosis brace according to an eighth embodiment of the present invention has an angle adjustment unit 806 having the same construction as the seventh embodiment described with reference to FIG. 10, except that the insertion hole 810 and the adjustment member 811 screw-coupled to it are installed on only one of the first and second rods 804 and 805. Details regarding limitation of rotation in one direction may be the same as described with regard to the sixth embodiment, and details regarding interlocking between the first and second rods 804 and 805 may be the same as described with regard to the third embodiment.

Figure 12A:
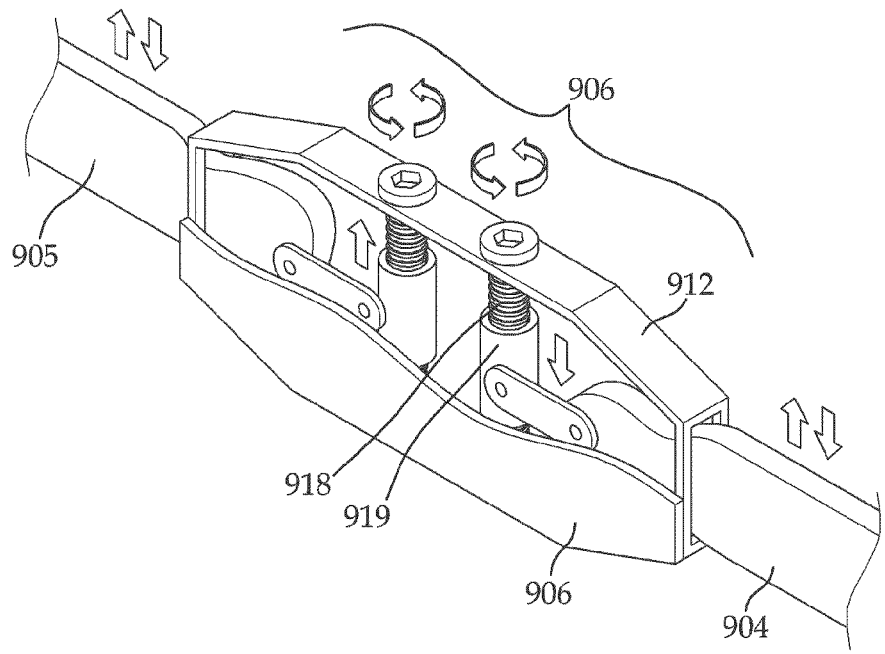
FIGS. 12A and 12B are a partially-broken perspective view and a sectional view of an angle adjustment unit of a scoliosis brace according to a ninth embodiment of the present invention, respectively.
Figure 12B:
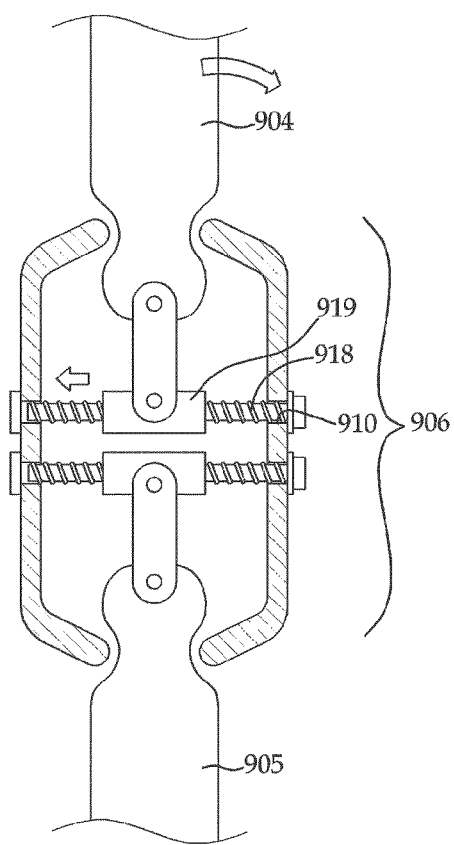

Referring to FIGS. 12A and 12B, a scoliosis brace according to a ninth embodiment of the present invention has an angle adjustment unit 906 configured in the following manner. The adjustment member, which is inserted into the insertion hole 910 to adjust the angle of at least one of the first and second rods 904 and 905, includes at least one male screw member 918 coupled to the insertion hole 910 so as to limit translation and allow rotation, and at least one female screw member 919 screw-coupled to the male screw member 918 so as to move linearly leftward/rightward as the male screw member 918 rotates. The female screw members 919 are connected to and interlocked with the first and second rods 904 and 905 so that, as the female screw members 919 move linearly, the first and second rods rotate and adjust their angle.

The first and second rods 904 and 905 have concave recesses formed on the other ends, respectively, and the recesses engage with openings of the base member 912 so that the first and second rods 904 and 905 are rotatably connected to the base member 912. The base member 912 has at least one insertion hole 910 formed on the lateral surface, and the male screw members 918 are simply inserted into the insertion holes 910, not screw-coupled to them, so as to extend through the base member 912. As a result, the male screw members 918 are allowed to rotate, but not to translate. The male screw members 918 extend through the insertion holes 910 to be screw-coupled to the female screw members 919 so that, as the male screw members 918 rotate, the female screw members 919 translate leftward/rightward. As a result, the first and second rods 904 and 905 connected to the female screw members 919 rotate and adjust their angle.

Figure 13:
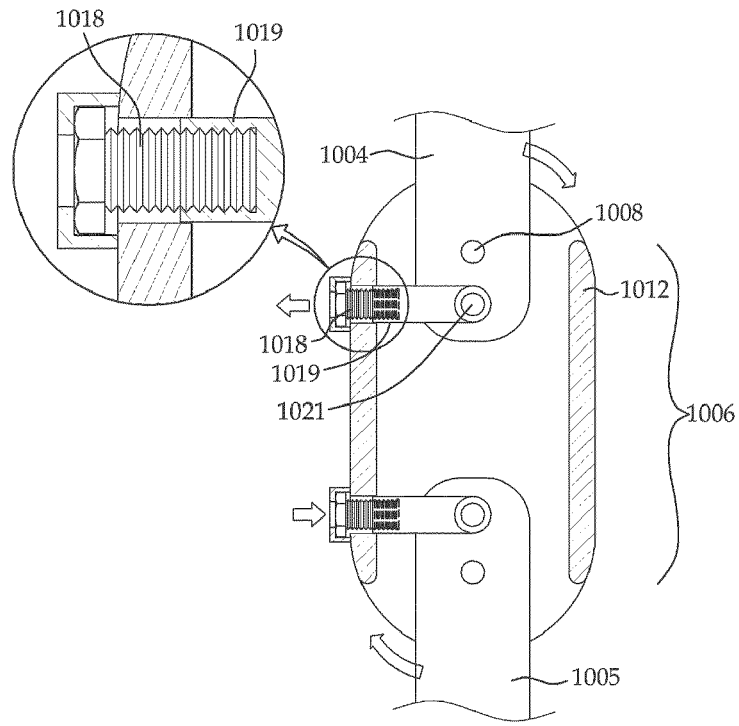
FIG. 13 is a sectional view briefly showing an angle adjustment unit of a scoliosis brace according to a tenth embodiment of the present invention.

Referring to FIG. 13, a scoliosis brace according to a tenth embodiment of the present invention has an angle adjustment unit 1006 having the same construction as the above-mentioned ninth embodiment except that one ends of the female screw members 1019 are rotatably connected to the other ends of the first and second rods 1004 and 1005, respectively.

The first and second rods 1004 and 1005 are rotatably connected to the base member 1012 by hinge shafts 1008, for example. The male screw members 1018 are inserted into the insertion holes 1010 and are allowed to rotate but not to translate. The male screw members 1018 are screw-coupled to the female screw members 1019, which are connected to and interlocked with the first and second rods 1004 and 1005 by hinge shafts 1021, for example.

As the male screw members 1018 rotate, the female screw members 1019 translate leftward/rightward, and the first and second rods 1004 and 1005 connected to the female screw members 1019 rotate and adjust their angle.

Figure 14:
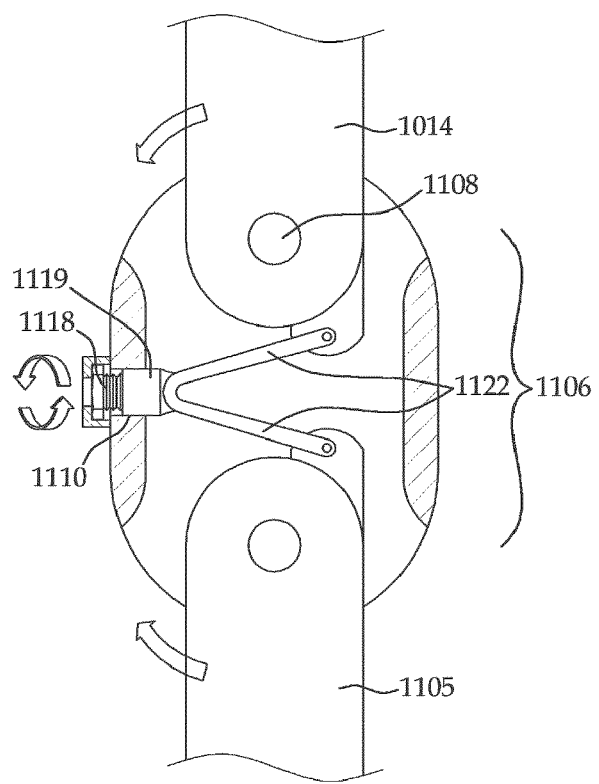
FIG. 14 is a sectional view briefly showing an angle adjustment unit of a scoliosis brace according to an eleventh embodiment of the present invention.

Referring to FIG. 14, a scoliosis brace according to an eleventh embodiment of the present invention has an angle adjustment unit 1106 having the same construction as the above-mentioned tenth embodiment except that one end of the female screw member 1119 is divided into two branches, which are rotatably connected to the other ends of the first and second rods 1104 and 1105, respectively.

As the male screw member 1118 rotates, the female screw member 1119 translates leftward/rightward. As a result, the first and second rods 1104 and 1105, which are connected by the connection units 1122 branching off from one end of the female screw member 1119, rotate and adjust their angle. As such, the first and second rods are operated simultaneously.

Figure 15:
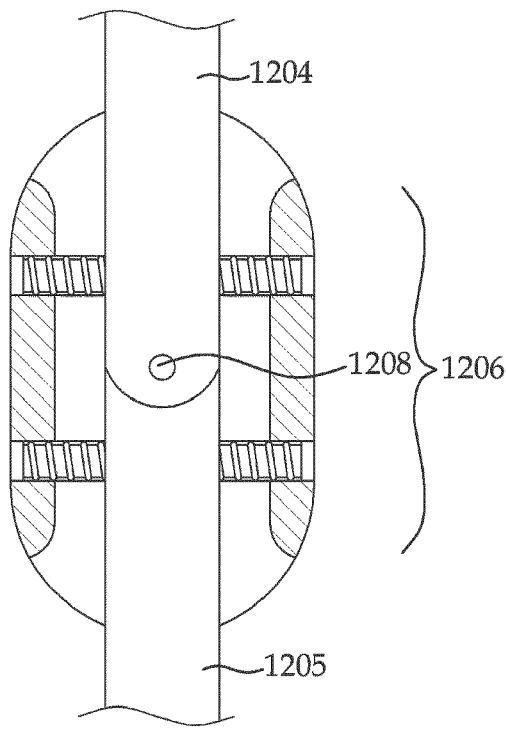
FIG. 15 is a sectional view briefly showing an angle adjustment unit of a scoliosis brace according to a twelfth embodiment of the present invention.

Referring to FIG. 15, a scoliosis brace according to a twelfth embodiment of the present invention has first and second rods 1204 and 1205 connected to a single hinge shaft 1208.

Except that the first and second rods 1204 and 1205 are connected to a single hinge shaft 1208, the construction according to the twelfth embodiment of the present invention is the same as the above-mentioned embodiment. According to the twelfth embodiment, the first and second rods 1204 and 1205 are connected to the same hinge shaft 1208. As a result, the number of necessary hinge shafts 1208 is reduced, and the angle adjustment unit 1206 has a simpler construction. This makes fabrication easier and reduces the possibility of malfunctioning.

Figure 16A:
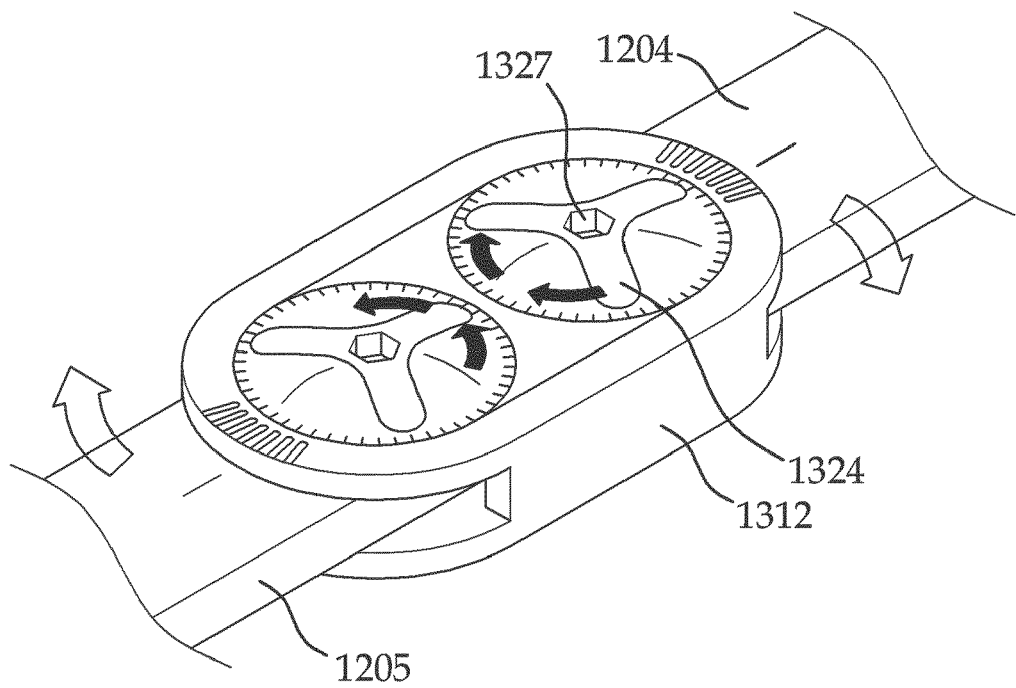
FIGS. 16A and 16B are a perspective view and a sectional view briefly showing an angle adjustment unit of a scoliosis brace according to a thirteenth embodiment of the present invention, respectively.
Figure 16B:
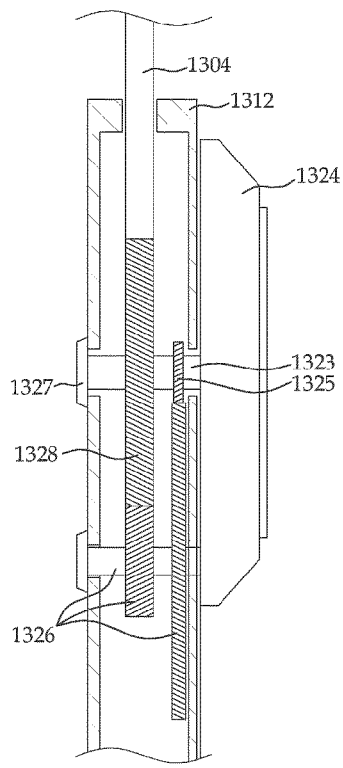

Referring to FIGS. 16A and 16B, a scoliosis brace according to a thirteenth embodiment of the present invention has an angle adjustment unit 1306 including a base member 1312 to which the other ends of the first and second rods 1304 and 1305 are rotatably connected, respectively; dial handles 1324 rotatably installed on the base member 1312 by means of shaft members 1323; gears 1325 fixed to the shaft members 1323; reduction gear units 1326 selectively connected to the gears 1325; and fixing members 1327 for selectively fixing the dial handles 1324 to the base. The other end of at least one of the first and second rods 1304 and 1305 is gear-coupled to the gears 1325 fixed to the shaft members 1323 or to the reduction gear units 1326.

According to an alternative embodiment, shaft members 1323 are installed in the inner space of the base member 1312, and are fixed to the base member 1312. Alternatively, female screws are formed inside the shaft members and are integrated with the fixing members 1327. Male screws are fastened at the center of the dial handles 1324 to fix them. In this case, the shaft members 1323 also play the role of the fixing members 1327.

The dial handles 1324 are rotatably installed on the shaft members 1323 outside the base member 1312, and the gears 1325 are fixed to the shaft members 1323. The other ends of the first and second rods 1304 and 1305 are provided with gears 1328, which directly mesh with the gears 1325 installed on the shaft members 1323 (not shown in the drawings) or mesh with separate reduction gear units 1326. The first and second rods 1304 and 1305 are rotatably connected to the base member 1312 by separate hinge shafts. Alternatively, the first and second rods 1304 and 1305 have through-holes, to which the shaft members 1323 are fitted so that the first and second rods 1304 and 1305 can rotate about the shaft members 1323 without being fixed to them.

If the thirteenth embodiment employs reduction gear units 1326, they include at least one reduction gear and gear shaft.

Adjustment of the gear ratio between the gears 1328 formed on the other ends of the first and second rods 1304 and 1305 and the gears 1325 fixed to the shaft members 1323 or adjustment of the reduction ratio of the reduction gear units 1326 ensures more detailed and accurate adjustment of the angle of the first and second rods 1304 and 1305.

Figure 17:
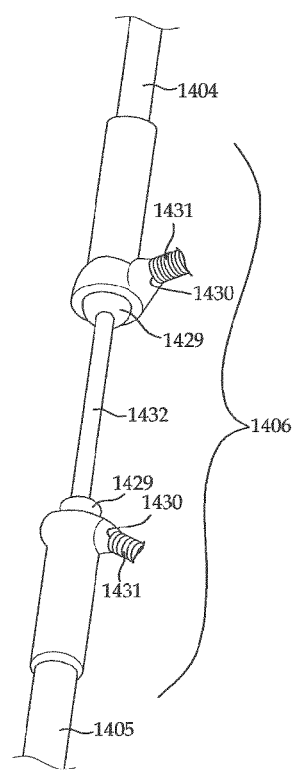
FIG. 17 is a sectional view briefly showing an angle adjustment unit of a scoliosis brace according to a fourteenth embodiment of the present invention.

Referring to FIG. 17, a scoliosis brace according to a fourteenth embodiment of the present invention has an angle adjustment unit 1406 including ball joints 1429, fixing screws 1431 for fixing the ball joints 1429, and fixing screw insertion holes 1430 to which the fixing screws 1431 are inserted.

The other ends of the first and second rods 1404 and 1405 are connected to the angle adjustment unit including the ball joints 1429 so that they can freely rotate in any direction (i.e. angle adjustment is easy). The ball joints 1429 have fixing screw insertion holes 1430 formed on one side so that the fixing screws 1431 are screw-coupled to them to fix the ball joints 1429. This guarantees that, after desired angle adjustment, the first and second rods 1404 and 1405 can be fixed. One or more ball joints may be used.

A ball joint support member 1432 may be used to connect between the ball joints 1429. Alternatively, the ball joints 1429 are either directly attached to the middle support unit or fixed to the base member attached to the middle support unit.

Figure 18A:
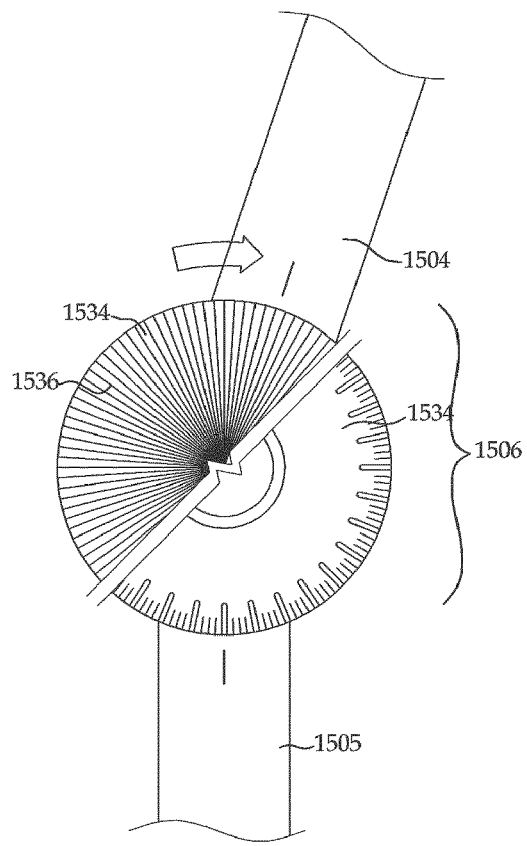
FIGS. 18A-18C are a partially-broken top view, an exploded perspective view, and an exploded sectional view briefly showing an angle adjustment unit of a scoliosis brace according to a fifteenth embodiment of the present invention, respectively.
Figure 18B:
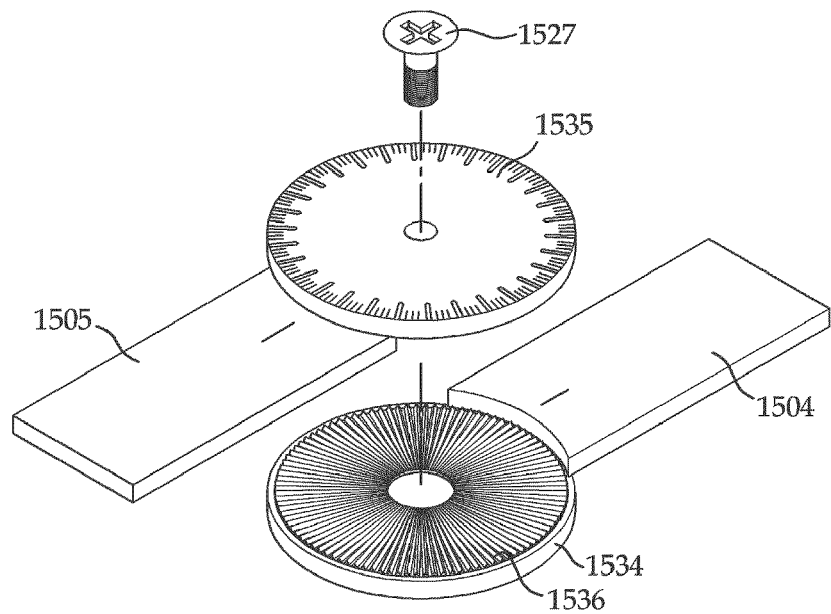
Figure 18C:
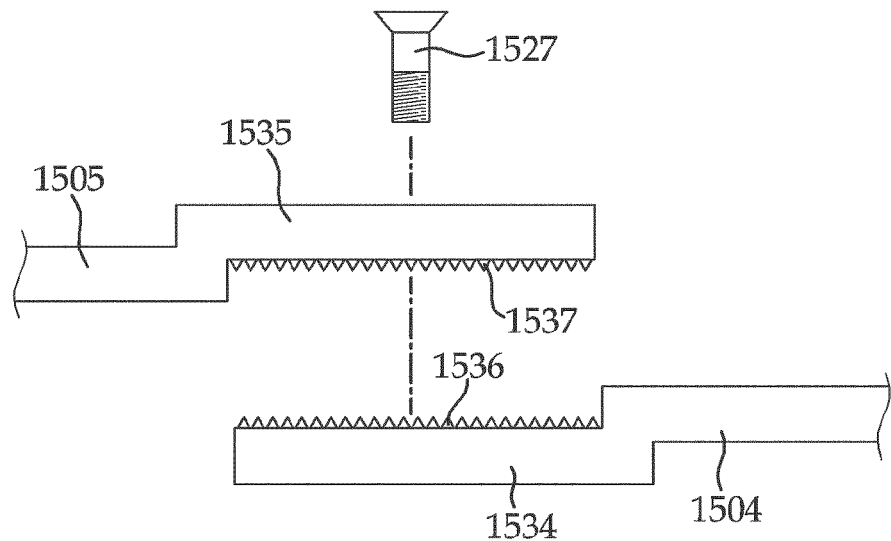

Referring to FIGS. 18A-18C, a scoliosis brace according to a fifteenth embodiment of the present invention has an angle adjustment unit 1506 including a first adjustment plate 1534 lying on the other end of the first rod 1504 and having first teeth 1536 formed on one surface in the radial direction; a second adjustment plate 1535 lying on the other end of the second rod 1505 and having second teeth 1537 formed on a surface, which faces the surface of the first adjustment plate 1534, so as to correspond to the first teeth 1536; and a fixing member 1527 for fixing the first and second adjustment plates 1534 and 1535.

Particularly, the angle adjustment unit 1506 has first and second adjustment plates 1534 and 1535 extending from the other ends of the first and second rods 1504 and 1505 in a predetermined shape, preferably a disk shape. First and second teeth 1536 and 1537 extend from the center of surfaces of the first and second adjustment plates 1534 and 1535, which face each other, in the radial direction so that the facing surfaces mesh with each other. The first and second adjustment plates 1534 and 1535 are meshed with each other so that the first and second rods 1504 and 1505 have a predetermined angle, and the first and second adjustment plates are fixed by the fixing member 1527 (e.g. a fixing screw screw-coupled through screw holes formed at the center of the adjustment plates). If the angle of the first and second rods 1504 and 1505 is to be readjusted, the fixing member 1527 is unfastened, and the first and second adjustment plates 1534 and 1535 are meshed with each other at the desired angle and are coupled again by the fixing member 1527.

Figure 19:
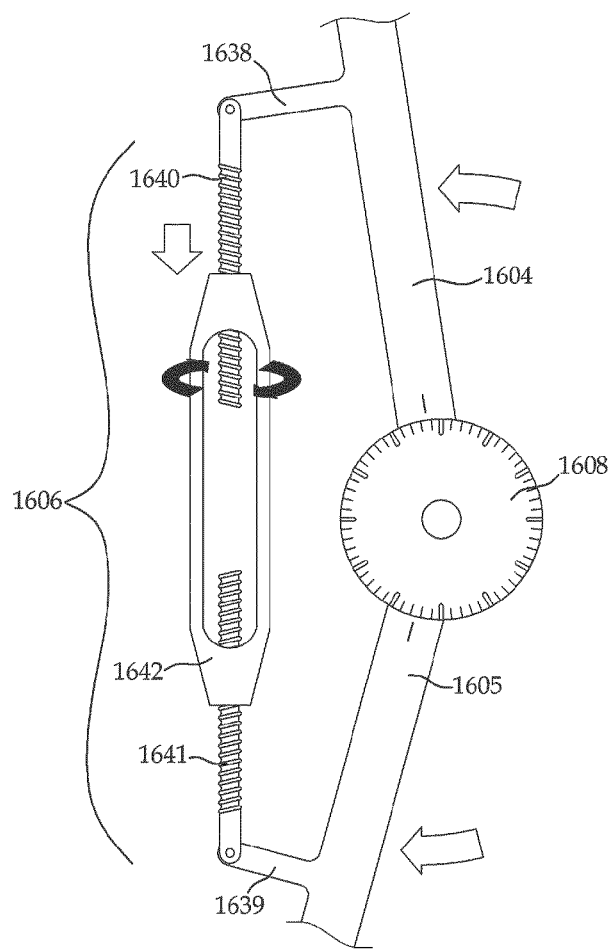
FIG. 19 is a front view briefly showing an angle adjustment unit of a scoliosis brace according to a sixteenth embodiment of the present invention.

Referring to FIG. 19, a scoliosis brace according to a sixteenth embodiment of the present invention has an angle adjustment unit 1606 including a hinge shaft 1608 to which the first and second rods 1604 and 1605 are rotatably connected; a first male screw member 1640 having one end rotatably connected to a first extension 1638 extending from one side of the first rod 1604; a second male screw member 1641 having one end rotatably connected to a second extension 1639 extending from one side of the second rod 1605; and a female screw member 1642 screw-coupled to the first and second male screw members 1640 and 1641. The first and second male screw members 1640 and 1641 are moved away from or toward each other according to the direction of rotation of the female screw member 1642 so that the angle of the first and second rods 1640 and 1605 is adjusted.

The first and second rods 1604 and 1605 are rotatably connected by a hinge shaft 1608, for example. The angle adjustment unit 1606 may be connected by extensions 1638 and 1639 which are separate from the hinge shaft 1608 and which extend from one sides of the first and second rods 1604 and 1605, respectively. One ends of the first and second male screw members 1640 and 1641 are rotatably connected to the extensions, respectively, and the other ends of the first and second male screw members 1640 and 1641 are screw-coupled to a single female screw member 1642. Rotation of the female screw members 1642 is followed by translation of the first and second male screw members 1640 and 1641. If the first and second male screw members 1640 and 1641 have right-handed and left-handed threads, respectively, rotation of the single female screw member 1642 is followed by movement of the first and second male screw members 1640 and 1641 away from or toward each other. As a result, the first and second extensions 1638 and 1639 are simultaneously pulsed or pushed so that angle of the first and second rods 1604 and 160 is adjusted based on interlocking between them.

Figure 20:
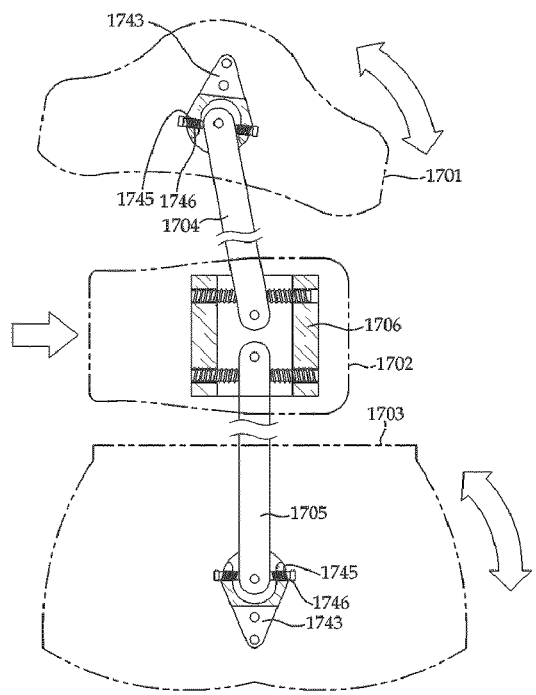
FIG. 20 briefly shows a scoliosis brace according to a seventeenth embodiment of the present invention.
Figure 21:
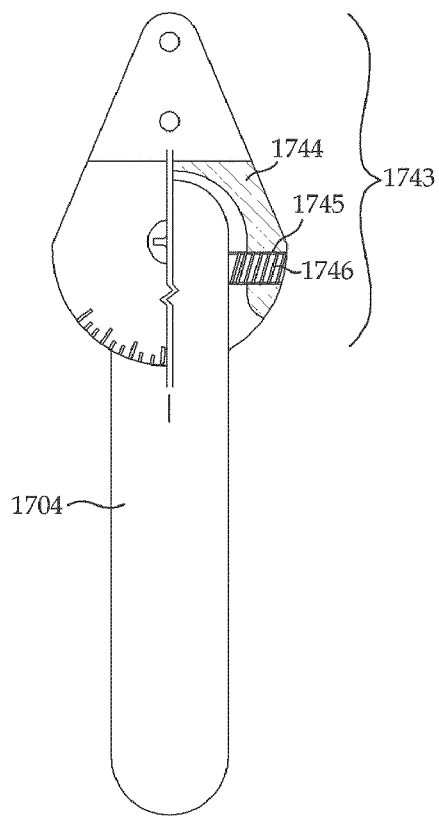
FIG. 21 is a partially-broken front view of a fixing unit of the scoliosis brace shown in FIG. 20.

Referring to FIGS. 20 and 21, a scoliosis brace according to a seventeenth embodiment of the present invention has a fixing unit 1743 including a fixing unit base 1744, which is attached to at least one of the upper and lower support units 1701 and 1073, to which one end of the first or second rod 1704 or 1705 is rotatably connected, and which has at least one insertion hole 1745 formed thereon; and a fixing member 1746 inserted into the insertion hole 1745 to fix the first or second rod 1704 or 1705.

The upper support unit 1701 and the first rod 1704 are connected by the fixing unit 1743, and the fixing unit base member 1744 attached to the upper support unit 1701 has at least one insertion hole 1745 formed thereon. The fixing member 1746 is inserted through the insertion hole 1745 to prevent the first rod 1704 from moving. If the fixing member 1746 is a fixing screw, it is screw-coupled to the female thread formed inside the insertion hole 1745 to fix the first rod 1704.

The same fixing unit may be used to connect the lower support unit 1703 and the second rod 1705.

The fixing unit 1743 is adapted not only to fix the first and second rods 1704 and 1705, but also to adjust the angle of the first and second rods 1704 and 1705. Particularly, by modifying the position of the fixing members 1746 inserted into both sides of the fixing unit 1743, the angle of the first and second rods 1704 and 1705 is adjusted. If the fixing members 1746 are fixing screws, the angle of the rods can be adjusted by fastening/unfastening the screws to the desired extent.

After the above-mentioned angle adjustment, the upper and lower support units 1701 and 1703 are not necessarily perpendicular to the rods or parallel with the middle support unit 1702. That is, the upper and lower support units 1701 and 1703 may be fixed at a desired angle as shown in FIG. 20 so that various types of correction methods can be practiced according to the patient's condition.

As in the case of the above-mentioned first embodiment, the fixing members 1746 inserted into both sides of the fixing unit 1743 may be unfastened so that the upper and/or lower support unit is allowed to rotate to some extent. As a result, the brace wearer can move more freely and lessen the constraint resulting from wearing the brace to some extent.

In the case of a scoliosis brace according to an eighteenth embodiment of the present invention, the first rod 104, the second rod 105, and the angle adjustment unit 106 may be made of a carbon material. Among the components of the scoliosis brace, the upper support unit 101, the middle support unit 102, and the lower support unit 103 are generally made of plastic, for example. However, the first rod 104, the second rod 105, and the angle adjustment unit 106 may be made of metal (e.g. iron, stainless steel) to withstand the weight of the human body, pressure, etc. However, this is inconvenient because the patient must remove the scoliosis brace to receive medical tests (e.g. X-ray photography).

Therefore, if the first rod 104, the second rod 105, and the angle adjustment unit 106 are made of carbon as in the case of the eighteenth embodiment, the patient can receive medical tests without removing the brace. However, those skilled in the art can understand that carbon is only an example, and the first rod 104, the second rod 105, and the angle adjustment unit 106 may be made of plastic having strength enough to withstand the weight of the human body, pressure, etc.

Figure 22:
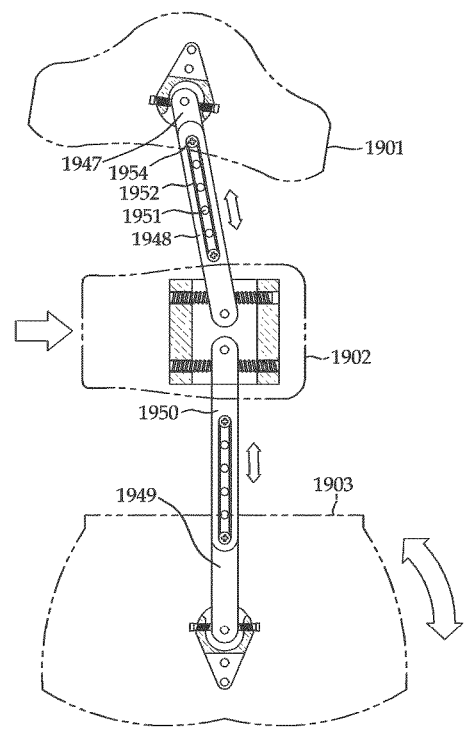
FIG. 22 briefly shows a scoliosis brace according to a nineteenth embodiment of the present invention.
Figure 23:
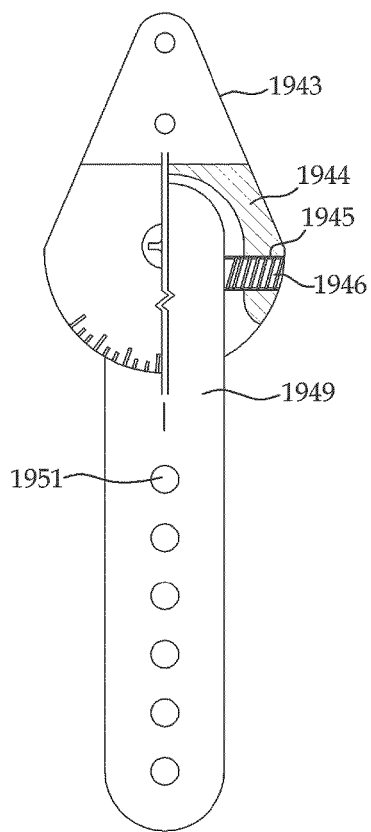
FIG. 23 is a partially-broken front view briefly showing a fixing unit and a first rod of the scoliosis brace shown in FIG. 22, which are coupled to each other.
Figure 24:
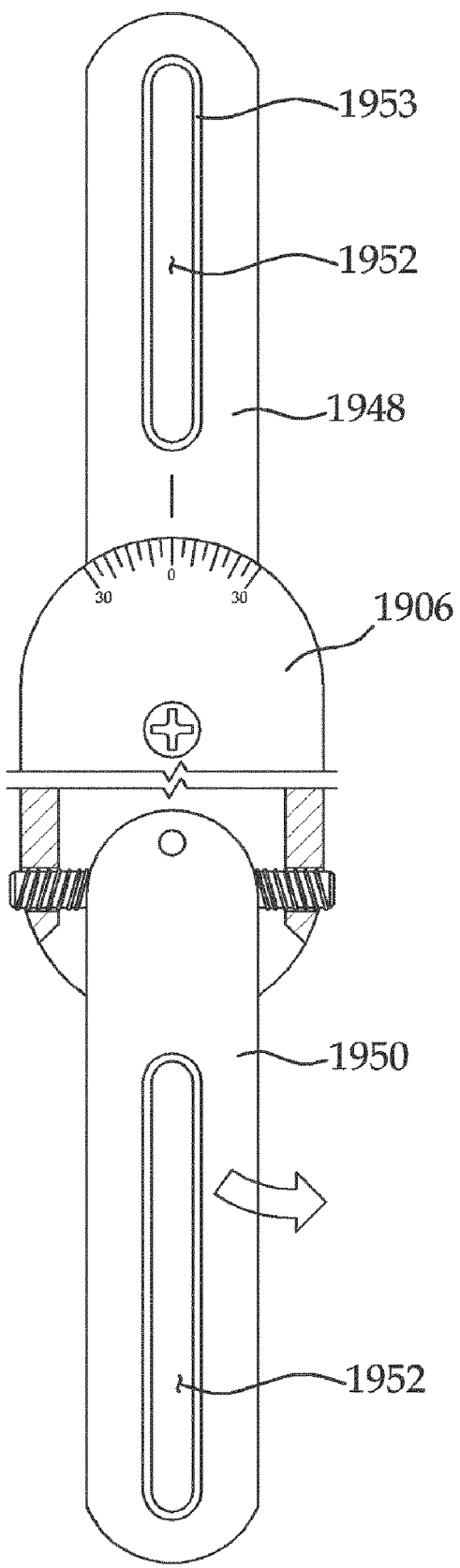
FIG. 24 is a partially-broken front view briefly showing an angle adjustment unit, a second rod, and a fourth rod of the scoliosis brace shown in FIG. 22, which are coupled to one another.

Referring to FIGS. 22-24, a scoliosis brace according to a nineteenth embodiment of the present invention is configured in the following manner to adjust the distance between the upper support unit 1901, the middle support unit 1902, and the lower support unit 1903.

Particularly, the scoliosis brace includes an upper support unit 1901; a middle support unit 1902; a lower support unit 1903; a first rod 1947 which has one end rotatably connected to the upper support unit 1901 and which includes length adjustment means 1951 and 1952; a second rod 1948 which has one end rotatably connected to an angle adjustment unit 1906 attached to the middle support unit 1902 and which is coupled to the first rod 1947 via the length adjustment means 1951 and 1952 so that the length can be adjusted; a third rod 1949 which has one end rotatably connected to the lower support unit 1903 and which includes length adjustment means 1951 and 1952; a fourth rod 1950 which has one end rotatably connected to the angle adjustment unit 1906 attached to the middle support unit 1902 and which is coupled to the third rod 1949 via the length adjustment means 1951 and 1952 so that the length can be adjusted; and an angle adjustment unit 190 which is attached to the middle support unit 1952 and to which the other ends of the second and fourth rods 1948 and 1950 are rotatably connected so that the rotation angle of the second and fourth rods 1948 and 1950 can be adjusted.

The first and second rods 1947 and 1948 have a plurality of length adjustment holes 1951 formed at an interval in the longitudinal direction of the rods and a length adjustment elongated hole 1952 formed in the longitudinal direction of the rods, respectively, as the first length adjustment means. The third and fourth rods 1949 and 1950 have a plurality of length adjustment holes 1951 formed at an interval in the longitudinal direction of the rods and a length adjustment elongated hole 1952, respectively, as the second length adjustment means. However, the rods and the combination of the length adjustment means are not limited to those shown in FIGS. 22-24, and the combination of the length adjustment holes 1951 and the length adjustment elongated hole 1952 may be switched. It is also possible to couple length adjustment holes 1951 to each other, or to couple length adjustment elongated holes 1952 to each other.

The first and third rods 1947 and 1949 are rotatably connected to the upper and lower support units 1901 and 1003 by conventional hinge shafts of fixing units 1943, for example, respectively. The second and fourth rods 1948 and 1950 are rotatably connected by the angle adjustment unit 1906 attached to the middle support unit. Details regarding fixing or angle adjustment of the rods by the fixing units 1943 and the angle adjustment unit 1906 have already been described, and repeated description thereof will be omitted herein.

A method for adjusting the length of the scoliosis brace according to the present invention will be described with reference to FIGS. 22-24, which employs a combination of length adjustment holes 1951 and a length adjustment elongated hole 1952 as the length adjustment means.

The first and second rods 1947 and 1948 are positioned so that the plurality of length adjustment means 1951, which are formed on the first rod 1947 at an interval in the longitudinal direction, overlap the length adjustment elongated hole 1952 formed on the second rod 1948 in the longitudinal direction. The overlapping part is adjusted to obtain the desired length. Then, at least one of the length adjustment holes 1951, preferably at least two length adjustment holes 1951 are coupled and fixed to the length adjustment elongated hole 1952 by a fastening means. The distance between the upper, middle, and lower support units of the scoliosis brace can be adjusted in this manner.

The fastening means may be a combination of a bolt and a nut. If the length adjustment holes 1951 have female threads formed on the inside, the first and second rods are overlapped so that the length adjustment elongated hole 1952 is positioned on top of the length adjustment holes 1951. Then, male screws are screw-coupled to the length adjustment holes 1951 through the length adjustment elongated hole 1952. A stepped portion 1953 for fixing the fastening means may be formed along the length adjustment elongated hole 1952 so that the male screws are coupled more firmly. The same construction may be applied to the third and fourth rods.

The angle adjustment unit 106 according to any of the above-mentioned embodiments may additionally have an angle indication scale on its outside to be visually recognized. Furthermore, the first and second rods 104 and 105 may have reference lines so that the angle can be recognized more precisely. Although this construction is shown in FIGS. 16A, 18A, 18B, 19, 21, 23, 24, etc., the same construction can be applied to other embodiments.

FIGS. 25-27B briefly show a scoliosis brace according to a twentieth embodiment of the present invention.

Figure 25:
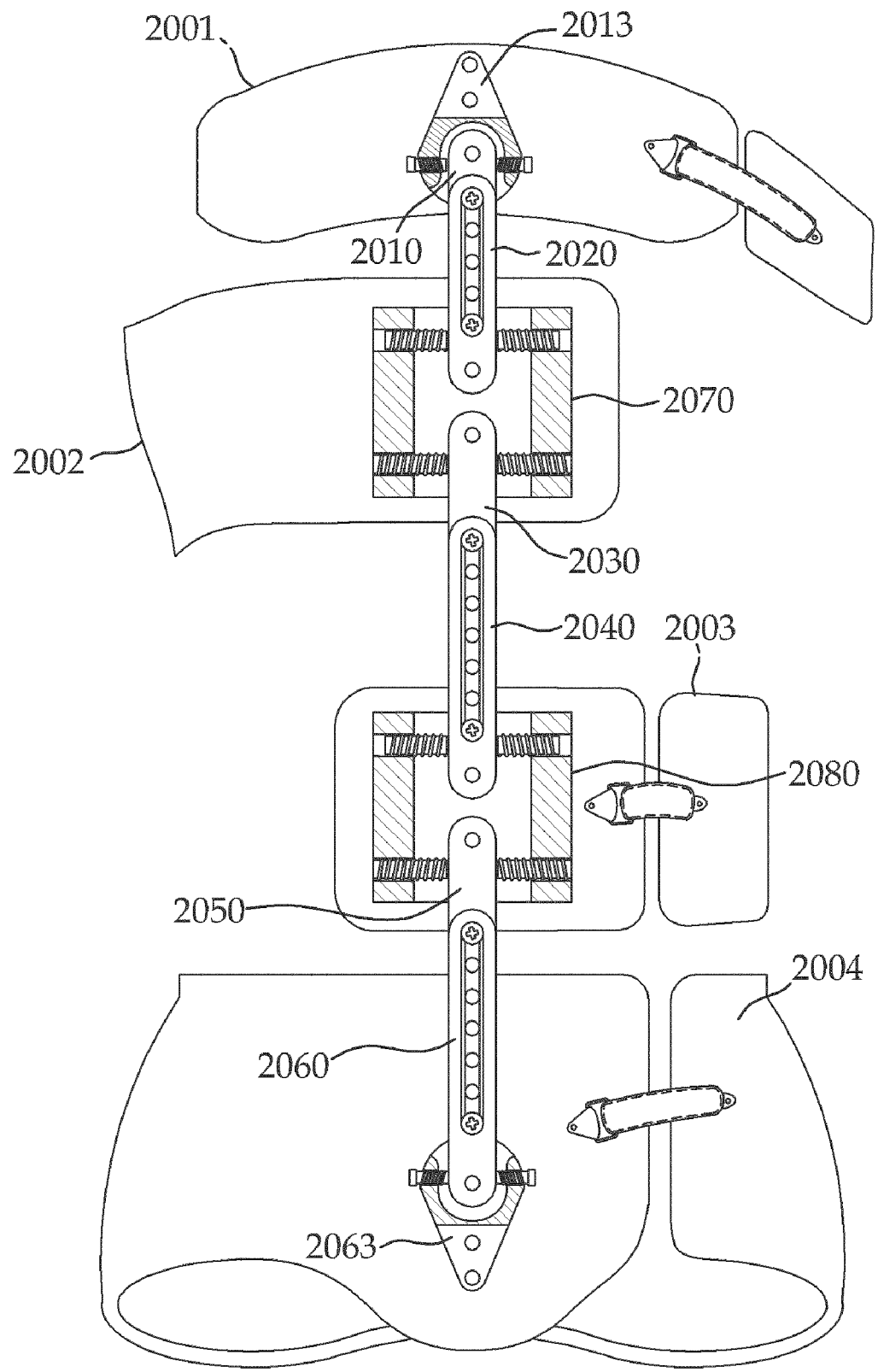
FIG. 25 is a partially-broken front view briefly showing a scoliosis brace according to a twentieth embodiment of the present invention.

Referring to FIG. 25, the scoliosis brace according to the twentieth embodiment of the present invention is different from the above-mentioned first to nineteenth embodiments in that it includes four support units 2001, 2002, 2003, and 2004 connected so as to move relative to one another. More particularly, the scoliosis brace according to the twentieth embodiment of the present invention includes an upper support unit 2001 for supporting the upper body UB (refer to FIG. 27B), a first middle support unit 2002 for supporting the upper part of the middle body MB, i.e. upper middle body UMB, a second middle support unit 2003 for supporting the lower part of the middle body MB, i.e. lower middle body LMB, and a lower support unit 2004 for supporting the lower body LB. The support units 2001, 2002, 2003, and 2004 are connected so as to move relative to one another. More particularly, the support units 2001, 2002, 2003, and 2004 are connected so that they can move relative to one another not only in the leftward/rightward direction, but also in the upward/downward direction.

Figure 27A:
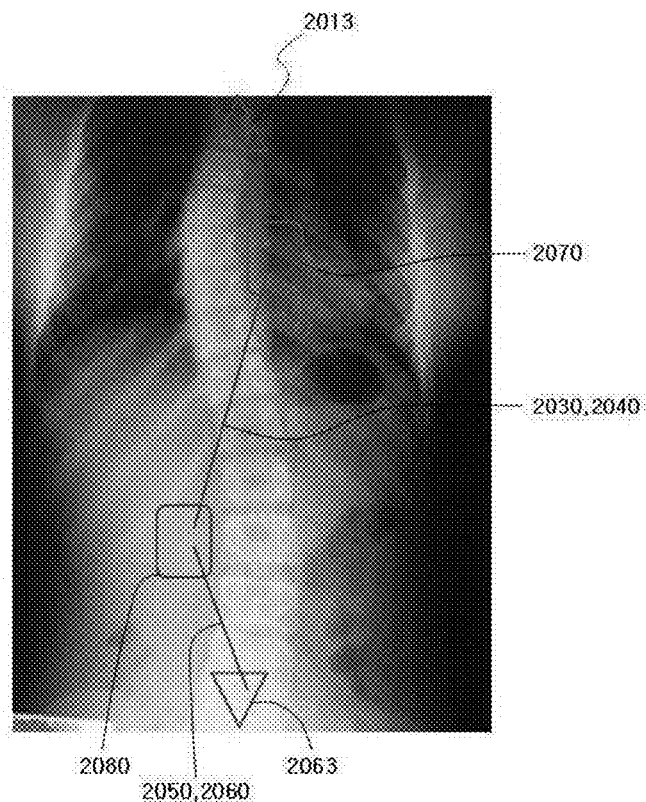
FIG. 27A is an X-ray photograph of a scoliosis patient with correction positions superimposed thereon to illustrate the correction process using the scoliosis brace shown in FIG. 25.

Such a connection of the four support units 2001, 2002, 2003, and 2004 while allowing relative movement guarantees that four points of the body can be pressurized. In other words, the spinal column can be corrected more precisely and efficiently than the above-mentioned first to nineteenth embodiments. For example, assuming that the spinal column is curved in an S-shape as shown in FIG. 27A, the spinal column can be corrected more efficiently and precisely when four points of the body are pressurized than when three points are pressurized. Particularly, the support units 2001, 2002, 2003, and 2004 can move relative to one another in the leftward/rightward direction so that pressure applied to the spinal column by the support units 2001, 2002, 2003, and 204 can be adjusted. In other words, pressure applied to the spinal column is optimized according to the curvature of the spinal column. Furthermore, the support units 2001, 2002, 2003, and 2004 can move relative to one another in the upward/downward direction to modify their relative positions and to determine the best points to pressurize, considering that each patient's spinal column is curved at different locations.

The coupling between respective support units 2001, 2002, 2003, and 2004 while allowing relative movements is made by first to sixth rods 2010, 2020, 2030, 2040, 2050, and 2060, first and second angle adjustment units 2070 and 2080, and first and second fixing units 2013 and 2063, which will now be described in detail.

One end of the first rod 2010 is rotatably installed on the upper support unit 2001, and the other end thereof is coupled to one end of the second rod 2020 by a fastening means (e.g. a plurality of through-holes formed at an interval or an elongated hole, and a bolt) so that the length can be adjusted in the longitudinal direction. More particularly, one end of the first rod 2010 is rotatably installed on the first fixing unit 2013, which is attached to the first upper support unit 2001, and the first rod 2001 is fixed at an angle adjusted by the first fixing unit 2013. The first fixing unit 2013 may have the same structure as in the case of the seventeenth embodiment (refer to FIG. 20), and detailed description thereof will be omitted herein.

The other end of the second rod 2020 is rotatably connected to the first angle adjustment unit 2070 which is attached to the first middle support unit 2002. Although it has been assumed that the first angle adjustment unit 2070 has the same structure as the angle adjustment unit according to the first embodiment, as shown in FIGS. 25-27B, it is also possible to apply the structure of the angle adjustment unit according to one of the second to nineteenth embodiments. The structure and principle of adjusting the angle of the first and second rods 2010 and 2020 by the first angle adjustment unit 2070 are the same as the first embodiment, and detailed description thereof will be omitted herein. The first and second rods 2010 and 2020 are coupled so that rotation relative to each other is limited.

One end of the third rod 2030 is rotatably connected to the first angle adjustment unit 2070 and is fixed after the rotation angle is adjusted by the first angle adjustment unit 2070.

As in the case of the first and second rods 2010 and 2020, one end of the fourth rod 2040 is connected to the other end of the third rod 2030 so that the length can be adjusted in the longitudinal direction, and the other end of the fourth rod 2040 is rotatably connected to the second angle adjustment unit 2080 attached to the second middle support unit 2003 so that the rotation angle of the third and fourth rods 2030 and 2040 can be adjusted and fixed. The third and fourth rods 2030 and 2040 are coupled so that rotation relative to each other is limited. Therefore, the first and second angle adjustment units 2070 and 2080 must adjust the rotation angle so that the third and fourth rods 2030 and 2040 rotate together in the same direction. The second angle adjustment unit 2080 may have the same structure and function as the above-mentioned first angle adjustment unit 2070, and detailed description thereof will be omitted herein.

One end of the fifth rod 2050 is rotatably connected to the second angle adjustment unit 2080 so that the rotation angle is adjusted by the second angle adjustment unit 2080 and fixed. The other end of the fifth rod 2050 is connected to one end of the sixth rod 2060 so that the length can be adjusted in the longitudinal direction. The connection structure between the fifth and sixth rods 2050 and 2060 may be the same as that between the first and second rods 2010 and 2020, and detailed description thereof will be omitted herein.

The other end of the sixth rod 2060 is rotatably connected to the lower support unit 2004. More particularly, the other end of the sixth rod 2060 is rotatably installed on the second fixing unit 2063 attached to the lower support unit 2004, and the sixth rod 2060 is rotated by a predetermined angle and fixed by the second fixing unit 2063. The second fixing unit 2063 may have the same structure as the first fixing unit 2013, and detailed description thereof will be omitted herein.

The process of operating the scoliosis brace, which has the above-mentioned construction, will now be described.

Figure 26:
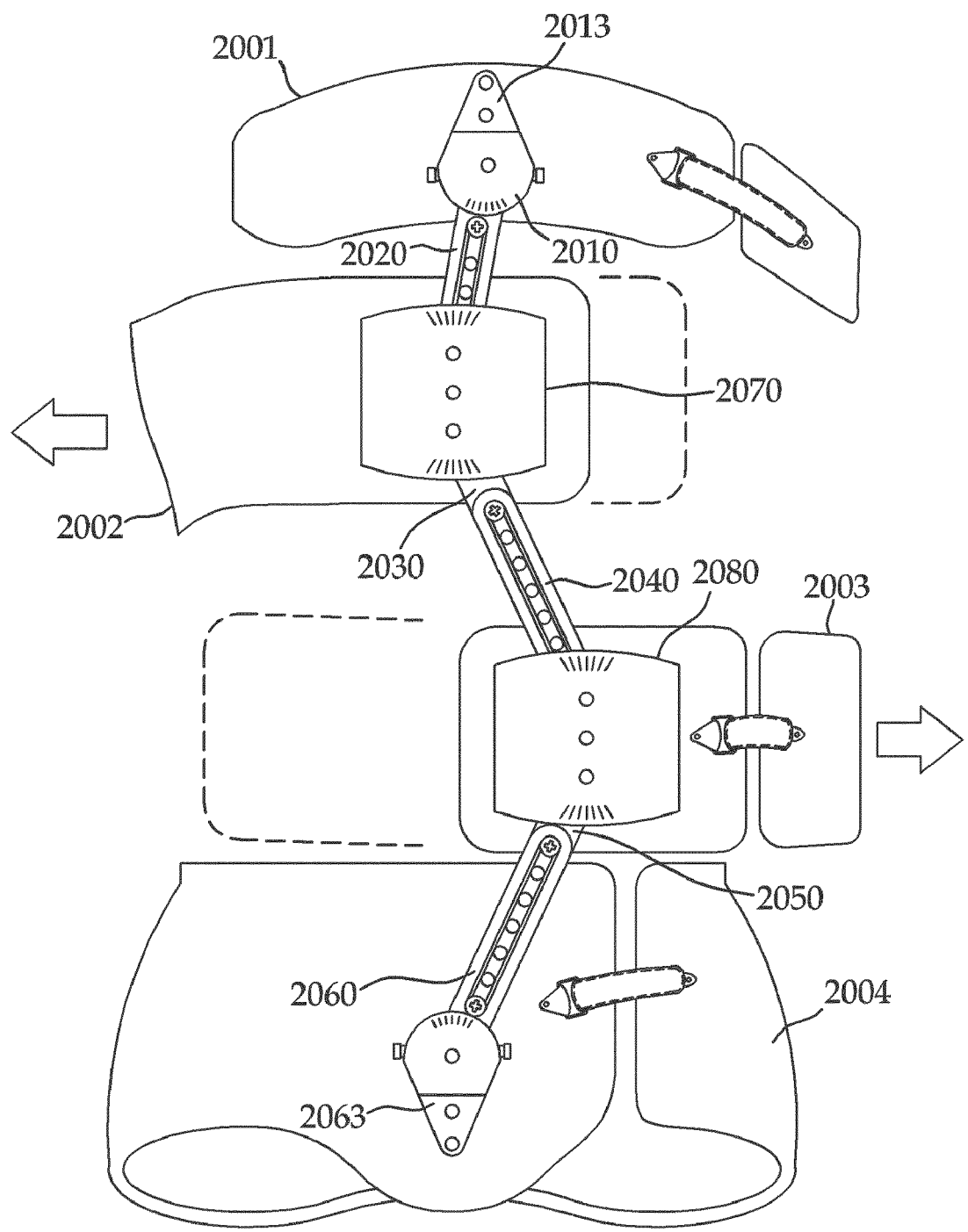
FIG. 26 is a front view illustrating the process of operating the scoliosis brace shown in FIG. 25.

FIG. 26 shows the process of operating the scoliosis brace having the above-mentioned construction. Referring to FIG. 26, the patient wears the scoliosis brace, and points on the patient's spinal column, which are to be pressurized, are determined. Based on the determined points, the length of the first and second rods 2010 and 2020 is adjusted. In addition, the length of the third and fourth rods 2030 and 2040, as well as that of the fifth and sixth rods 2050 and 2060, is adjusted. Then, the first and second angle adjustment units 2070 and 2080 are operated to adjust the angle of the first to sixth rods 2010, 2020, 2030, 2040, 2050, and 2060. In addition, the first and second fixing units 2013 and 2063 are operated to fix the angle of the first and second rods 2010 and 2020, and that of the fifth and sixth rods 2050 and 2060.

Figure 27B:
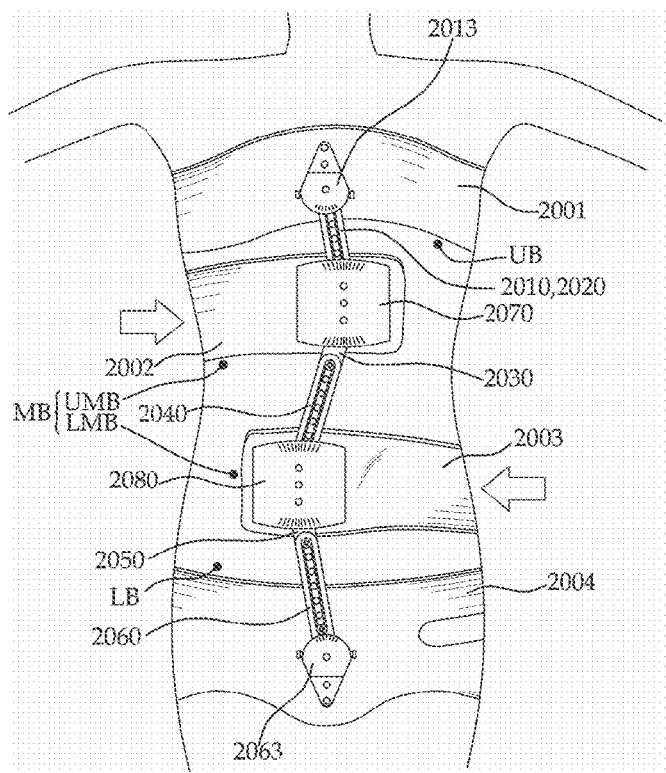
FIG. 27B briefly shows a scoliosis brace worn by the scoliosis patient shown in FIG. 27A.

FIG. 27A is an X-ray photograph of a scoliosis patient, and briefly shows the position of the first and second angle adjustment units 2070 and 2080 for correcting the spinal column. Particularly, the first and second angle adjustment units 2070 and 2080 are positioned so that the first middle support unit 2002 pressurizes the leftward-curved part of the spinal column to the right, and the second middle support unit 2003 pressurizes the rightward-curved part of the spinal column to the left. As such, the spinal column is corrected efficiently with regard to the curved parts. FIG. 27B briefly shows the scoliosis brace worn by a patient.

Figure 28A:
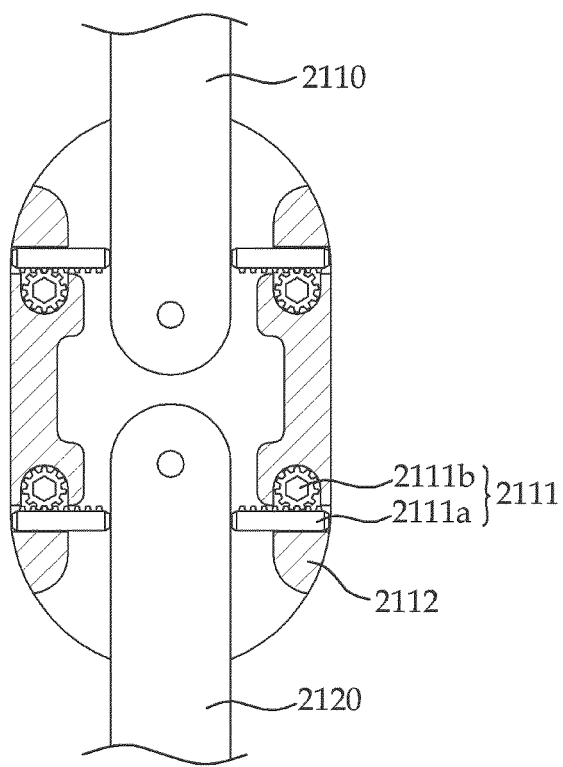
FIGS. 28A and 28B briefly show an angle adjustment unit of a scoliosis brace according to a twenty-first embodiment of the present invention.
Figure 28B:
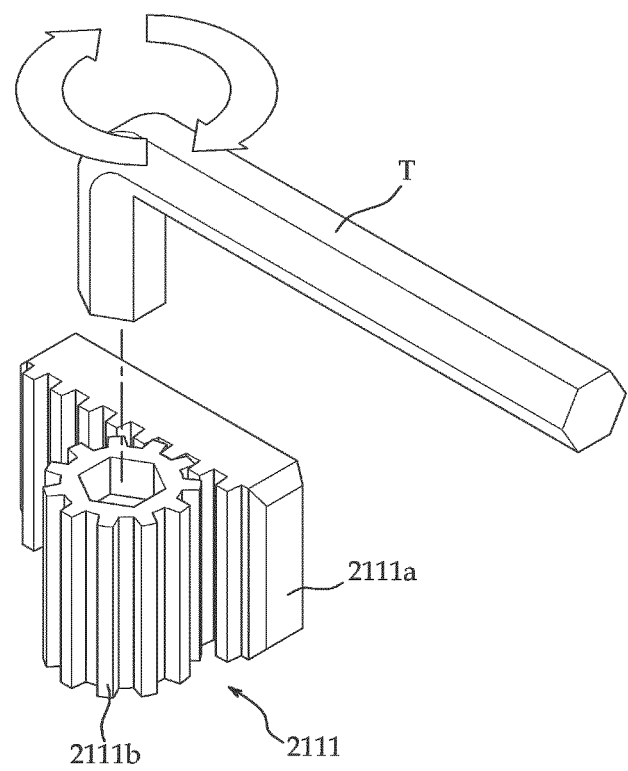

FIGS. 28A and 28B show major parts of a scoliosis brace according to a twenty-second embodiment of the present invention. Referring to FIGS. 28A and 28B, the base member 2112 is provided with an adjustment member 2111 so that the angle of the rods 2110 and 2120 can be adjusted in front of the angle adjustment unit according to the twenty-second embodiment of the present invention. More particularly, the adjustment member 2111 according to the twenty-second embodiment of the present invention includes a first member 2111a installed on the base member 2112 so as to move leftward/rightward to pressurize the rods 2110 and 2120, and a second member 2111b connected to the first member 2111a to move it leftward/rightward and arranged on the base member 2112 in the forward/backward direction.

The first member 2111a is installed on the base member 2112 so as to move leftward/rightward and pressurize respective rods 2110 and 2120, the angle of which is thus adjusted. Those skilled in the art can understand that, although the first member 211a consists of a rack according to the present embodiment, any type of member may be employed as long as it can convert rotational movements into linear movements.

The second member 2111b is rotatably installed on the base member 2112 and arranged in the forward/backward direction. As mentioned above, the second member 2111b is gear-connected to the first member 2111a to move it leftward/rightward. The second member 2111b consists of a pinion according to the present embodiment. The second member 2111b has a hexagonal adjustment recess formed on its upper surface, as shown in FIG. 28B, so that it can be rotated by an adjustment tool T (e.g. hexagonal wrench).

According to this construction, rotation of the second member 2111b is followed by leftward or rightward movement of the first member 2111*a*, which meshes with the second member 2111*b*. Then, respective rods 2110 and 2120 are pressurized and rotated so that their rotation angle is adjusted. As such, the rotation angle of respective rods 21110 and 2120 can be adjusted in front of the angle adjustment unit by the first and second members 2111*a* and 2111*b*. In other words, the rotation angle of respective rods 2110 and 2120 can be adjusted in a more convenient and precise manner.

Although it has been assumed in the present embodiment that the first and second members 2111*a* and 2111*b* are a rack and a pinion meshing with each other, any type of members may be employed as long as the rotational movement of the base member 2112 about the rotational axis in the forward/backward direction into a linear movement in the leftward/rightward direction.

The scoliosis brace according to the present invention is equipped with an angle adjustment unit for easily adjusting the angle between the upper and middle support units and the angle between the lower and middle support units. This makes it possible to easily adjust the correction angle of the scoliosis brace according to the patient's condition. Furthermore, more diversified correction methods are provided than conventional braces, and scoliosis patients are treated more efficiently.

The inventive scoliosis brace can maintain a desired correction angle. This guarantees constant pressurization and better correction effects. The inventive scoliosis brace is of a three-piece type (i.e. upper, middle, and lower support units) so that three points (i.e. thorax, loin, and sacrum) of the spinal column can be pressurized. This ensures better correction effects.

The correction angle can be simply adjusted while the patient wears the inventive brace. This makes it possible to modify the correction method as the patient's condition improves or worsens. The brace can be adapted to limit movement in only one direction and allow movement in the other direction. Then, the brace wearer can move more freely to lessen the constraint resulting from wearing the brace and stretch muscles. This multiplies the treatment effects.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A scoliosis brace comprising:
   a plurality of support units for supporting different parts of a human body, said plurality of support units comprising
      an upper support unit for receiving and supporting the upper part of the body;
      a middle support unit for receiving and supporting the middle part of the body; and
      a lower support unit for receiving and supporting the lower part of the body,
      wherein respective support units are connected to one another so that relative positions can be modified, and the upper, middle, and lower parts of the body are pressurized according to relative positions of respective support units, to generate pressurization force for correcting the spinal column,
   at least one first rod having a first end rotatably connected to the upper support unit;
   at least one second rod having a first end rotatably connected to the lower support unit; and
   an angle adjustment unit attached to the middle support unit, second ends of the first and second rods being rotatably connected to the angle adjustment unit, respectively, so that rotation angles of the first and second rods can be adjusted.

2. The scoliosis brace as claimed in claim 1, wherein the angle adjustment unit comprises:
   a base member having at least one insertion hole formed thereon, the second ends of the first and second rods being rotatably connected to the base member, respectively; and
   an adjustment member inserted into the insertion hole to adjust the angle of at least one of the first and second rods.

3. The scoliosis brace as claimed in claim 2, wherein the adjustment member is screw-coupled to the insertion hole to move linearly in a leftward/rightward direction according to the direction of rotation thereof, and at least one of the first and second rods is pressurized by the leftward/rightward movement of the adjustment member so that the angle is adjusted.

4. The scoliosis brace as claimed in claim 3, wherein the first and second rods are coupled to and interlocked with each other.

5. The scoliosis brace as claimed in claim 3, wherein the adjustment member is coupled to the insertion hole so that rotation of the first and second rods in a predetermined direction is allowed but rotation in other directions is limited.

6. The scoliosis brace as claimed in claim 2, wherein the adjustment member comprises:
   at least one male screw member coupled to the insertion hole so that translation is limited and only rotation is allowed; and
   at least one female screw member screw-coupled to the male screw member to move linearly leftward/rightward as the male screw member rotates, wherein the female screw member is connected to and interlocked with the first and second rods so that, as the female screw member moves linearly, the first and second rods rotate and the angle is adjusted.

7. The scoliosis brace as claimed in claim 1, wherein the angle adjustment unit comprises:
   a base member, the second ends of the first and second rods being rotatably connected to the base member, respectively;
   a dial handle rotatably installed on the base member via a shaft member;
   a gear fixed to the shaft member;
   a reduction gear unit selectively connected to the gear; and
   a fixing member for selectively fixing the dial handle to the base member,
   wherein the second end of at least one of the first and second rods is gear-coupled to the gear fixed to the shaft member or to the reduction gear unit.

8. The scoliosis brace as claimed in claim 1, wherein the angle adjustment unit comprises a ball joint and a fixing screw for fixing the ball joint.

9. The scoliosis brace as claimed in claim 1, wherein the angle adjustment unit comprises:
   a first adjustment plate provided on the second end of the first rod, first teeth being formed on a surface of the first adjustment plate in a radial direction;
   a second adjustment plate provided on the second end of the second rod, second teeth being formed on a surface facing the surface of the first adjustment plate, the second teeth corresponding to the first teeth; and
   a fixing member for selectively fixing the first and second adjustment plates.

10. The scoliosis brace as claimed in claim 1, wherein the angle adjustment unit comprises:
- a hinge shaft for rotatably connecting the first and second rods;
- a first male screw member having a first end rotatably connected to a first extension extending from a first side of the first rod;
- a second male screw member having a first end rotatably connected to a second extension extending from a first side of the second rod; and
- a female screw member screw-coupled to the first and second male screw members,
- wherein the first and second screw members are moved away from or toward each other according to the direction of rotation of the female screw member to adjust the angle of the first and second rods.

11. The scoliosis brace as claimed in claim 1, further comprising:
- a fixing unit base member attached to at least one of the upper and lower support units, the first end of the first or second rod being rotatably connected to the fixing unit base member, at least one insertion hole being formed on the fixing unit base member; and
- a fixing unit inserted into the insertion hole formed on the fixing unit base member to fix the first or second rod.

12. The scoliosis brace as claimed in claim 1, wherein the first rod, the second rod, and the angle adjustment unit are made of a carbon material.

13. A scoliosis brace comprising:
- an upper support unit;
- a middle support unit;
- a lower support unit;
- an angle adjustment attached to the middle support unit to adjust the angle of the upper and lower support units with regard to the middle support unit;
- a first rod having a first side rotatably connected to the upper support unit, a first length adjustment means being positioned on a second side of the first rod;
- a second rod having a first side rotatably connected to the angle adjustment unit and a second side coupled to the first rod via the first length adjustment means so that the length can be adjusted;
- a third rod having a first side rotatably connected to the lower support unit, a second length adjustment means being positioned on a second side of the third rod; and
- a fourth rod having a first side rotatably connected to the angle adjustment unit and a second side coupled to the third rod via the second length adjustment means so that the length can be adjusted.

14. The scoliosis brace as claimed in claim 13, further comprising:
- a fixing unit base member attached to at least one of the upper and lower support units, the first end of the first or third rod being rotatably connected to the fixing unit base member, at least one insertion hole being formed on the fixing unit base member; and
- a fixing unit having a fixing member inserted into the insertion hole to fix the first or third rod.

15. A scoliosis brace comprising:
- an upper support unit for receiving and supporting an upper body of a person;
- a first middle support unit for receiving and supporting a first side of an upper middle body of the person, the first middle support unit being connected to the upper support unit so that the relative position can be changed;
- a second middle support unit for receiving and supporting a second side of a lower middle body of the person, the second middle support unit being connected to the first middle support unit so that the relative position can be changed; and
- a lower support unit for receiving and supporting a lower body of the person, the lower support unit being connected to the second middle support unit so that the relative position can be changed,
- a first rod having a first end rotatably installed on the upper support unit;
- a second rod having a first end connected to a second end of the first rod so that the length can be adjusted in the longitudinal direction;
- a first angle adjustment unit attached to the first middle support unit, a second end of the second rod being rotatably connected to the first angle adjustment unit so that the rotation angle of the second rod can be adjusted;
- a third rod having a first end rotatably connected to the first angle adjustment unit so that the rotation angle can be adjusted;
- a fourth rod having a first end connected to a second end of the third rod so that the length can be adjusted in the longitudinal direction;
- a second angle adjustment unit attached to the second middle support unit, a second end of the fourth rod being rotatably connected to the second angle adjustment unit so that the rotation angle of the fourth rod can be adjusted;
- a fifth rod having a first end rotatably connected to the second angle adjustment unit so that the rotation angle can be adjusted; and
- a sixth rod having a first end connected to a second end of the fifth rod so that the length can be adjusted in the longitudinal direction and a second end rotatably connected to the lower support unit,
- wherein the upper body, the upper middle body, the lower middle body, and the lower body of the person are pressurized according to the relative position of the upper support unit, the first middle support unit, the second middle support unit, and the lower support unit, respectively, to generate pressurization force for correcting the spinal column of the person,
- wherein the first middle support unit is connected to the upper support unit so that the relative position can be changed in the leftward/rightward and upward/downward directions,
- the second middle support unit is connected to the first middle support unit so that the relative position can be changed in the leftward/rightward and upward/downward directions, and
- the lower support unit is connected to the second middle support unit so that the relative position can be changed in the leftward/rightward and upward/downward directions.

* * * * *